United States Patent
Winqvist et al.

(10) Patent No.: US 7,951,365 B2
(45) Date of Patent: *May 31, 2011

(54) METHOD FOR EXPANSION OF TUMOUR-REACTIVE T-LYMPHOCYTES FOR IMMUNOTHERAPY OF PATIENTS WITH SPECIFIC CANCER TYPES

(75) Inventors: Ola Winqvist, Uppsala (SE); Magnus Thörn, Uppsala (SE)

(73) Assignee: Deifiera Falun AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 12/147,752

(22) Filed: Jun. 27, 2008

(65) Prior Publication Data

US 2009/0022695 A1    Jan. 22, 2009

Related U.S. Application Data

(60) Provisional application No. 60/937,484, filed on Jun. 27, 2007.

(51) Int. Cl.
*A01N 63/02* (2006.01)
*A61K 35/02* (2006.01)
*A61K 35/26* (2006.01)

(52) U.S. Cl. ............... 424/93.71; 424/534; 424/578

(58) Field of Classification Search ............ None
See application file for complete search history.

(56) References Cited

U.S. PATENT DOCUMENTS

| 7,012,098 B2 * | 3/2006 | Manning et al. ............... 514/562 |
| 2003/0129749 A1 * | 7/2003 | Gundersen et al. ......... 435/372.3 |
| 2006/0104950 A1 * | 5/2006 | Okano et al. ................. 424/93.2 |

FOREIGN PATENT DOCUMENTS

| WO | EP 1408106 | * 4/2004 |
| WO | WO2004/045650 | 6/2004 |

OTHER PUBLICATIONS

Ruttinger et al (Clinical and Experimental Metastasis, 2004, vol. 21, pp. 305-312).*
Kim et al (Cancer, 1999, vol. 86, pp. 22-30).*
Hedfords and Brinchman (Scandinavian Journal of Immunology, 2003, vol. 58, pp. 522-532).*

* cited by examiner

*Primary Examiner* — Karen A Canella
(74) *Attorney, Agent, or Firm* — Porter, Wright, Morris & Arthur LLP

(57) ABSTRACT

Methods for treating a patient suffering from a neoplastic disease are disclosed and described. A number of diseases can be treated under the present methods, including without limitation gall bladder cancer, hepato cellular cancer, ovarian cancer, small intestine cancer, lung cancer, mesothelioma, breast cancer, kidney cancer, pancreas cancer, prostate cancer, carcinoid cancer, leiomyosarcoma, or metastasis thereof. A general method for providing such treatment may include: 1) identifying in a patient one or more sentinel and/or metinel lymph nodes draining the neoplasm; 2) resecting the one or more nodes and, optionally all or part of the tumour or metastasis; 3) isolating tumour-reactive T-lymphocytes from said lymph nodes; 4) in vitro expanding said tumour-reactive T-lymphocytes; and 5) administering the thus obtained tumour-reactive T-lymphocytes to the patient.

31 Claims, 19 Drawing Sheets

A: Beginning

B: End

METHOD FOR EXPANSION OF TUMOUR-REACTIVE T-LYMPHOCYTES FOR IMMUNOTHERAPY OF PATIENTS WITH SPECIFIC CANCER TYPES

PRIORITY CLAIM

This application claims the benefit of earlier filed U.S. Provisional Application No. 60/937,484, filed Jun. 27, 2007, which is incorporated herein by reference.

FIELD OF THE INVENTION

The invention relates to an improved method for expansion and activation of tumour-reactive lymphocytes, in particular CD4+ helper and/or CD8+ T-lymphocytes. The T-lymphocytes are not CD4+ CD25+$^{Hi}$ lymphocytes, i.e. the present invention does not cover regulatory T-lymphocytes. The lymphocytes may be used for treating and/or preventing specific cancer types, in particular gall bladder cancer, hepato cellular cancer, ovarian cancer, small intestine cancer, lung cancer, mesothelioma, breast cancer, kidney cancer, pancreas cancer, prostate cancer, carcinoid cancer, leiomyosarcoma, or metastasis thereof.

BACKGROUND OF THE INVENTION

According to the immune surveillance hypothesis, the immune system is continuously sensitized against developing tumours, where experimental evidence strongly supports this notion. The identification of specific tumour antigens has created new possibilities for tumour immunotherapy and many immunotherapeutic approaches are now being translated into clinical trials. Among these, adoptive transfer of tumour antigen-specific lymphocytes seems particularly promising. These attempts have, so far, usually been based on either mononuclear cells from peripheral blood or tumour infiltrating lymphocytes (TIL) separated from fresh tumour specimens. In recent trials, treatment of patients with malignant melanoma with autologous transfer of expanded TILs, objective response rates of up to 51% has been reported. TIL cells are few, they are frequently unresponsive (anergic) due to immunosuppressive mechanisms from the tumour creating long periods for expansions to occur (several months). Furthermore, the protocols have been aiming towards the expansion of CD8+ cytotoxic T cells and the cells have been reintroduced into patients preconditioned with chemotherapy and in addition the patients have been treated with high doses of interleukin-2 to provide survival of CD8+ T cells.

Gallbladder Cancer

Gallbladder cancer is a relatively uncommon disease with approximately 9 000 new cases per year in the United States. Gallbladder cancer is very aggressive and commonly spreads to the liver, pancreas or stomach.

Patients diagnosed with gallbladder cancer face a grim prognosis with overall survival being only 5%-10%. In cases where the cancer has spread to other organs, long term survival is very rare.

The most common form of treatment today is surgical removal of the gallbladder and lymph node dissection.

Hepatocellular Carcinoma

Hepatocellular carcinoma is a malignant tumor of the liver. The disease accounts for approximately 19 000 new cases each year in the United States. Infection with the Hepatitis B och C viruses has been established as a major cause of the disease.

Prognosis of the disease is generally very poor. The most common form of treatment is surgical resection of the tumor, in cases where possible. If the cancer cannot be removed, the disease is usually deadly within 3 to 6 months.

Ovarian Cancer

Cancer of the ovaries accounts for approximately 27 000 new cases and 15 000 deaths per year in the United States. There are over 25 major types of ovarian neoplasms, the most common being serous adenocarcinoma.

Prognosis is very dependant upon in which stage the disease is diagnosed. For early stages, long-term survival can reach over 90%. Survival is dramatically decreased with later diagnosis, and overall five year survival for all stages is less than 40%.

Surgery is today the preferred form of treatment, with chemotherapy used after surgery to treat any residual disease.

Small Intestine Cancer

Small intestine cancer, or cancer of the small bowel, accounts for only a minute proportion of all gastrointestinal malignancies. There are approximately 6 000 new cases per year in the United States. Adenocarcinoma is the most common subtype of small intestine cancer, accounting for approximately half of the cases.

Inflammatory disease of the small bowel has been established as a major risk factor for small intestine cancer.

Surgery is today the only known effective treatment, and is possible in approximately two thirds of all patients. Five year survival rates for patients who undergo surgical resection of the tumor is 40-60%.

Breast Cancer

With almost 180 000 new cases per year, breast cancer is the most common type of cancer among women in the United States, and the second most common cause of cancer death (approximately 40 000 deaths per year). Over the last 50 years, the incidence of the disease has slowly increased.

Despite much research, the cause of breast cancer is still poorly understood.

For staging and prognosis, evaluation of tumor cell presence in regional lymph nodes is commonly done in conjunction with surgery.

Along with surgery, treatment alternatives include chemotherapy, hormonal therapy, radiotherapy and immune therapy.

Lung Cancer

Carcinoma of the lung is the most common cause of cancer death worldwide and in the United States. More than 200 000 new cases are developed each year in the United States, and about 160 000 will die from the disease.

Cigarette smoking is by far the leading cause of lung cancer, accounting for approximately 85% of all cases. All subtypes of lung cancer are associated with cigarette smoking, but the strongest connection is with squamos cell carcinoma and small cell carcinoma. In cases where the patient is a non-smoker, the most common type is adenocarcinoma.

Patients with surgically resectable tumors have the best prognosis. Factors correlated with adverse prognosis include large tumor size and metastases to lymph nodes.

Mesothelioma

Mesothelioma is a neoplasm of mesothelial cells, which is most common in the pleura. Approximately 2 000 patients are affected each year in the United States.

More than 80% of patients are reported to have been exposed to asbestos. The latency period between exposure and appearance of the disease is usually 20-40 years.

There are no known effective treatments today, and the prognosis is dismal.

Kidney Cancer

The most common type of kidney cancer is renal cell carcinoma, followed by renal pelvis carcinoma. Each year, there are in total more than 50 000 new cases of kidney cancer in the United States, and kidney cancer is the cause of more than 12 000 deaths.

In patients where the cancer has not spread to other organs, kidney cancer can normally be cured with surgery. If the cancer has spread to lymph nodes or other organs, commonly the lung, bone or liver, long-term is reduced dramatically to only around 10%.

Prostate Cancer

Prostate cancer is a very common malignancy among older men. Patients younger than 50 years constitute less than 1% of all new cases (about 220 000 each year) in the United States. Prostate cancer accounts for about 25 000 deaths every year in the U.S.

Almost all of primary prostatic tumors are adenocarcinomas. The most common metastatic sites are the lymph nodes, bonea, lung and liver.

Radiation therapy and surgical removal of the prostate are the most common forms of treatment today.

Carcinoid Cancers

Carcinoid is an often malignant type of tumor originating in the cells of the neuroendocrine system. The majority of carcinoid tumors are found in the appendix, small intestine or rectum. The tumor can also originate in other locations, including the lungs, pancreas, bronchus, gallbladder ovary and testis.

Surgical removal of the tumor is the standard treatment when possible and is often curative. Carcinoid tumors are generally slow-growing. In patients with distant metastases, the median survival is about two years.

Leiomyosarcoma

Leiomyosarcoma is a rare type of malignant neoplasm of smooth muscle. It can arise almost anywhere in the body, but most commonly in the uterus, abdomen or pelvis.

Radiation therapy and chemotherapy are usually ineffective against leiomyosarcoma. Surgical resection of the tumor can be curative. The five year survival rate for leiomyosarcoma is about 30%.

The immune system often appears informed about tumours, as shown by an accumulation of immune cells at tumour sites, which correlates with improved prognosis. Immuno-competent cells respond to "danger" signals, which can be provided of growing tumours as a consequence of the genotoxic stress of cell transformation and disruption of the surrounding microenvironment. Under ideal conditions, these signals will induce inflammation, activate innate effector cells with antitumour activity, and stimulate professional antigen-presenting cells (APCs), particularly dendritic cells (DCs), to engulf tumour-derived antigens and migrate to draining lymph nodes to trigger an adaptive response by T and B lymphocytes. Thus, the immune system is capable of recognizing and eliminating tumour cells but unfortunately tumours often interfere with the development and function of immune responses. However, recent advances in cellular and molecular immunology suggest strategies, which may prevent antitumour responses. Briefly, the presence of a tumour indicates that the developing cancer was able to avoid detection or to escape or to overwhelm the immune response. Progressing tumours often exhibit strategies that promote evasion from immune recognition. Examples are physical exclusion of immune cells from tumour sites, poor immunogenicity due to reduced expression of major histocompatibility complex (MHC) or costimulatory proteins, and disruption of natural killer (NK) and natural killer T (NKT) cell recognition. Further, some tumours prevent triggering of an inflammatory response by secreting proteins such as interleukin 10 (IL-10) or vascular endothelial growth factor (VEGF) that interfere with DC activation and differentiation, or by blocking the production of proinflammatory molecules by increasing expression of the STAT3 protein. Even if a response is induced, tumour cells may escape elimination by losing targeted antigens, rendering tumour-reactive T cells anergic, inducing regulatory T cells, or specifically deleting responding T cells. The tumour that finally develops reflects selection of poorly immunogenic and/or immune-resistant malignant cells.

In the adjuvant setting, tumour immunotherapy offers an appealing alternative to traditional cytostatics. One strategy has been to expand and activate NK cells in vitro with out specific antigen by culture with IL-2 followed by infusion of large numbers of these NK cells back into patients alone or with high doses of IL-2. This approach, or administration of high doses of IL-2 to expand and activate NK cells entirely in vivo, has yielded antitumour activity and remission in a subset of patients (Rosenberg S A et al., J Natl Cancer Inst 85, 622, 1993). However, life-threatening toxicity often develops, largely due to the release of tumour necrosis factor (TNF) from activated NK cells.

Thus, it is obvious that there is still a need for an effective and at the same time safe treatment of gall bladder cancer, hepato cellular cancer, ovarian cancer, small intestine cancer, lung cancer, mesothelioma, breast cancer, kidney cancer, pancreas cancer, prostate cancer, carcinoid cancer, leiomyosarcoma, or metastasis thereof.

DETAILED DESCRIPTION OF THE INVENTION

The present inventors have previously shown that activation of naïve T cells may occur within the highly specialized microenvironment of secondary lymphoid organs, such as the sentinel lymph node. In other words, the sentinel node may be regarded as the primary site for the immune system to encounter tumour antigens.

The inventors have previously disclosed a general method for expansion of tumour-reactive T-lymphocytes from sentinel lymph nodes, showing that it is possible to culture T-lymphocytes obtained from sentinel lymph nodes in order to obtain a culture of tumour-reactive T-lymphocytes. The tumour-reactive T-lymphocytes may be used for treating cancer by administering an effective amount of tumour-reactive T-lymphocytes to the patient from which the sentinel nodes were removed.

The success of a cancer treatment comprising administration of tumour-reactive T-lymphocytes are determined by factors such as, e.g., the amount of tumour-reactive T-lymphocytes obtained after the expansion step, i.e. the amount of tumour-reactive T-lymphocytes available for infusion to the patient, the time required to obtain an effective amount of tumour-reactive T-lymphocytes and the concentration and ratio of specific subpopulations of tumour-reactive T-lymphocytes obtained by the expansion method.

Accordingly, the present invention discloses an improved method for expansion of tumour-reactive CD4+ helper and/or CD8+ T-lymphocytes, wherein specific culturing conditions have been determined and optimized, and wherein specific markers on the T-lymphocytes and in the culture medium are monitored throughout the expansion phase, in order to obtain high numbers of tumour-reactive T-lymphocytes in the shortest possible time span. Furthermore, the invention at the same time provides a method for directing the development of tumour-reactive CD4+ helper and/or CD8+ T-lymphocytes towards specific subpopulations. The T-lymphocytes are not CD4+ CD25+$^{Hi}$ lymphocytes, i.e. the present invention does not cover regulatory T-lymphocytes.

CD4$^+$ CD25$^{Hi}$ T lymphocytes expressing the transcription factor FoxP3 are considered regulatory T cells (Treg). Tregs have the property to regulate T helper and T cytotoxic cells by inhibiting activation and proliferation and in addition Treg inhibit the production and release of useful Th1 cytokines such as IFN-gamma. Thus, the method presented here is developed in order to promote the expansion of T helper cells and T cytotoxic T cells and to avoid expansion of Treg cells.

The tumour-reactive T-lymphocytes most often generated by the present method are CD4+ helper T-lymphocytes. One of the objects of the present expansion method is in some respect to imitate the natural pathway of the patient's own immune system, and to a certain degree let the components of the patients immune system determine whether, in the first place, CD4+ helper or CD8+ T-lymphocytes are generated, depending on whether antigen is presented by MCHI or MCHII. In most cases, the antigens will be presented by the class II MCH molecule leading to generation of CD4+ helper T-lymphocytes. However, in some cases CD8+ T-lymphocytes are generated. If CD4+ helper T-lymphocytes are generated, they will be further expanded as described herein, however, the method may also be used for expanding CD8+ cells.

The inventors have found that an expansion method comprising two different phases are especially useful for obtaining a high number of tumour-reactive CD4+ helper and/or CD8+ T-lymphocytes in a relatively short time span, the two phases being
i) a first phase of stimulating tumour-reactive T-lymphocytes with tumour-derived antigen together with at least one substance having agonistic activity towards the IL-2 receptor, to promote survival of tumour-reactive T-lymphocytes, and
ii) a second phase of activating and promoting growth of tumour-reactive T-lymphocytes, wherein the second phase ii) is initiated when the CD25 cell surface marker (IL-2R marker) is down-regulated on T-lymphocytes.

This expansion method may also be carried out using monocytes isolated from the patient as antigen specific cells. The monocytes will be administered to the patient when differentiated into dendritic cells by the use of maturating cytokines such as IL-4, GM_CSF and IL-3 followed by activation of the dendritic cells by the addition of Toll like receptor stimulating agencies such as lipopolysaccharide. The use of mature activated dendritic cells as the antigen specific population may promote and enhance the expansion of T helper cells and T cytotoxic T cells.

DEFINITIONS

By the term "tumour-reactive T-lymphocytes" is intended to mean T-lymphocytes carrying a T cell receptor specific for and recognizing a tumour antigen.

By the term "T helper cells" is intended to mean T-lymphocytes that promote adaptive immune responses when activated.

By the term "Th1 cells" is intended to mean T helper cells that promote cell mediated immune responses when activated, using cytokines such as IFN-gamma.

By the term "Th2 cells" is intended to mean T helper cells promoting humoral immune responses when activated, using cytokines such as IL-4.

By the term "CD4+ helper T-lymphocytes" is intended to mean T-lymphocytes that express CD4 but not the transcription factor FoxP3.

By the term "CD8+ T-lymphocytes" is intended to mean T-lymphocytes that express CD8.

By the term "regulatory T-lymphocyte" is intended to mean T-lymphocytes that suppress adaptive immune responses, expressing transcription factor FoxP3.

By the term "specific activation" of T-lymphocytes is intended to mean antigen specific and MHC restricted T-cell receptor mediated activation. In contrast the term "unspecific activation" of T-lymphocytes is intended to mean a general activation of all T-cells, regardless of T-cell receptor specificity.

The term "tumour-derived antigen" intends to cover tumour cells, a homogenate of a tumour, which homogenate may be denatured, or tumour proteins, polypeptides or peptides, e.g. in the form of purified, natural, synthetic and/or recombinant protein, polypeptide or peptide. The tumour-derived antigen may be intact molecules, fragments thereof or multimers or aggregates of intact molecules and/or fragments. Examples of suitable polypeptides and peptides are such that comprises from about 5 to about 30 amino acids, such as, e.g. from about 10 to 25 amino acids, from about 10 to 20 amino acids or from about 12 to 18 amino acids. If peptides are used, a final molar concentration in the culture of from about 0.1 to about 5.0 µM, such as, e.g., from about 0.1 to about 4.0 µM, from about 0.2 to about 3.0 µM, from about 0.3 to about 2.0 µM or from about 0.3 to about 1.0 µM may be used. The tumour-derived antigen may be autologous or heterologous, i.e. arise from the patient to be treated or be obtained from another subject suffering from cancer. In the present Examples the inventors uses an autologous denatured tumour extract, however, as mentioned above, other sources of the tumour-derived antigen may also be feasible for use in a method according to the invention.

By the term "day 1 of the first phase" or e.g. "day 5 of the second phase" is to be understood the following: The day on which the lymphocytes are harvested is denoted day 0 (zero). Day 1 of the first phase is defined as the day where the expansion is initiated by addition of at least one substance having agonistic activity towards the IL-2 receptor, and maybe culture medium and/or tumour-derived antigen. The expansion phase i) may be initiated on day 0 (zero) or up till 2 days after harvest of the lymphocytes. The day on which the second phase is initiated by addition of tumour-derived antigen is throughout the text described as "day 1 of the second phase".

By the term "sentinel lymph node" is intended to mean the first lymph node(s) to receive lymphatic drainage from a tumour. The term "metinel lymph node" refers to the first lymph node(s) to receive lymphatic drainage from a metastasis.

By the term "V beta profile" or "V beta repertoire" is intended to mean the distribution of groups of T cells expressing identical Vbeta domains of the T cell receptor complex in a population of cells.

The first step in the present method is the identification of one or more sentinel or metinel lymph nodes draining a tumour in a gall bladder cancer, hepato cellular cancer, ovarian cancer, small intestine cancer, lung cancer, mesothelioma, breast cancer, kidney cancer, pancreas cancer, prostate cancer, carcinoid cancer, leiomyosarcoma, or metastasis thereof. The step i) of identifying one or more sentinel or metinel nodes are crucial for the method according to the invention, as the present inventors have shown that these nodes comprises a high amount of T-lymphocytes activated against tumour-derived antigens in vivo.

One way of identifying the sentinel or metinel lymph node is by injecting one or more lymph node locators into the patient, i.e. any substances suitable for locating a lymph node. Such locators are preferably pharmaceutically acceptable and/or biocompatible. The locators can either be affinity based or non-affinity based. Examples of affinity based lymph node locators are antibodies in whole or fragments, nanobodies, nucleic acids such as RNA, DNA, and PNA all of which can be in turn labeled using various detection modalities. Detection of affinity based lymph node locators can be done by labeling with tracers and dyes, such as, e.g., the ones mentioned below. Visualization is then made by i) radiological methods such as x-ray, computerized tomography, scintigraphy, positron emission technique after labeling with contrast generating substances, such as, e.g., iodine containing substances or radioactive substances such as, e.g. technetium-99m, ii) magnetic resonance imaging after labeling with magnetic or paramagnetic substances, such as e.g., gadolinium, magnetodendromers or iron oxide containing particle; iii) light in the IR-visible-UV spectra by labeling with dyes, fluorescent dyes or luminescent dyes for detection by the naked eye or photon detecting devices such as CCD or CMOS sensors.

Examples of non-affinity based lymph node locators encompass tracers and dyes. These substances are transported in the lymph capillaries and accumulate through phagocytosis by macrophages in the sentinel or metinel node(s), thus identifying the tumour or metastasis draining lymph node(s).

Examples of tracers are radioactive substances such as, e.g., technetium-99 for radioactive decay based detection with photon sensitive films or sensors such as PET detectors. Further on magnetic, paramagnetic or superparamagnetic substances, such as, e.g., gadolinium containing contrast agents, iron oxide particles, magnetic oxide particles, magnetodendrimers for magnetic resonance based detection, contrast agents, such as, e.g., iodine for radiological based detection such as, e.g., computerized tomography or regular X-ray may be used.

Examples of dyes encompasses e.g., azo dyes, bisazo dyes, triazo dyes, diaryl methan dye, triaryl methan dye, anthrachino dye, polycyclic aromatic carbonyl dyes, indigo dyes for visualization by luminescence, near infrared, fluorescence, UV and visible light. Further on dyes also encompass luminescent substances for luminescence based detection and fluorescent substances, such as, e.g., pico green, sybr green, red O oil, texas red for fluorescence based detection. Detection can depending on the chosen wavelengths be made either by the naked eyes or photon detecting devices such as CCD or CMOS sensors.

In one embodiment the dye has an emission maximum that permits visualization by the naked eye in normal light. In another embodiment the dye has an emission maximum that permits visualization by the naked eye in UV light.

Other examples of suitable dyes or tracers appear from WO 04/045650, which is hereby incorporated by reference.

Another, but far more time-consuming way to identify sentinel or metinel nodes is to remove and investigate a selection of lymph nodes in the presumed tumour or metastasis area. A tumour extract from the tumour or metastasis of the actual patient could then be used to identify lymph nodes containing tumour-reactive T-lymphocytes by proliferating assays.

The lymph node locators are injected into the patient into, above, around, adjacent and/or under the tumour or metastasis. The locator will then spread through lymph vessels leading into the metinel lymph node(s), and the one or more nodes will start to get stained within a certain period of time, such as, e.g. within 5 min to 30 min, such as, e.g. within 5 min to 15 min after injection of the locator substance, where after the locator substance is imaged. As described above, imaging of the locator is of course dependent on the locator substance used.

If a dye having an emission maximum that allows visualization by the naked eye in normal light is used, such as, e.g. Patent Blue, the one or more sentinel or metinel nodes are simply identified as the nodes, which are first to accumulate the coloured dye, i.e. if Patent Blue is used, the surgeon will look for the lymph nodes first to accumulate a blue colour.

The locators may be injected by a single injection or by multiple injections, such as, e.g., by two or more injections, by three or more injections, by four or more injections, by five or more injections or by six or more injections.

How to perform the injections of the lymph node locators is dependent on the location of the tumour or metastasis.

The lymph node locators may be injected involving a surgical procedure, i.e. a procedure that includes an incision. In such cases, the surgeon will perform an incision in the area of the tumour and subsequently, a lymph node locator may be injected directly into, above, around, adjacent and/or under the metastasis in order to identify the one or more sentinel lymph nodes.

The lymph node locators may also be injected by a non-surgical procedure, i.e. a procedure that does not involve a surgical step, wherein a surgical step is defined a one including surgical operative procedures, i.e. involving incisions with an instrument. In the present context, an injection, i.e. the punctuation of the skin with a needle, is not considered a surgical step. Accordingly, by the statement that the lymph node locator may be injected by a non-surgical procedure is intended to mean that the lymph node locator may be injected into, above, around, adjacent and/or under the metastasis directly into or through the skin.

Examples of situations wherein the lymph node locators may be injected into or through the skin, is e.g. cases where metastasis of tumours are located in the skin of the patient. In such situations the lymph node locator should preferentially be injected into the skin above the metastasis, or through the skin into, around, adjacent and/or under the metastasis. If the metastasis is located in the breast area of the patient, the lymph node locator should preferentially be injected into the skin above the metastasis, or through the skin into, around, adjacent and/or under the metastasis.

The metinel lymph nodes may not always be placed at the shortest or most logical anatomical distance from the metastasis. Accordingly, as a metinel lymph node may be placed distant from the metastasis, it may in some cases be very beneficial to inject a lymph node locator without the need for surgery, as it may be very difficult to predict the position of such a metinel lymph node, and there by difficult to predict the place in the body to perform the surgery to remove the metinel node. In a specific embodiment of the invention, the lymph node locator is a radioactive substance, such as, e.g. technetium-99m, which may be injected by a non-surgical procedure, and later imaged by performing a lymphoscintigraphy.

Some times the identification of the metinel lymph nodes may involve injection of lymph node locators by a combination of a non-surgical and a surgical step. As an example of this a radioactive lymph node locator, such as, e.g., technetium-99m may be injected using a needle, i.e. without the need for surgery, and the accumulation of the locator, i.e. identification of the metinel node(s) may be performed using a gamma detector. This gives the surgeon an indication towards where the metinel nodes are located. Later on, when the patient is undergoing surgery to have the metinel lymph nodes and at least part of metastasis removed, a coloured dye such as, e.g., Patent Blue Dye may be injected. Furthermore, if there is a lapse of more than about 18 to 24 hours after the first injection, it might be beneficial to add one or more extra injections with radioactive tracer dependent on the half-life of the radioactive tracer (usually about 6 hours) in order to identify the metinel nodes during surgery.

After having located the one or more sentinel or metinel lymph nodes by one or the other method, the surgeon will remove these in order to investigate whether the sentinel or metinel lymph nodes contain any tumour cells, and in order to obtain a culture of tumour-reactive T-lymphocytes.

The harvesting of lymphocytes from the one or more sentinel or metinel lymph nodes may be performed by homogenizing the sentinel or metinel lymph node material in order to obtain single cell suspensions of lymphocytes. The single cell suspensions may then be subjected to in vitro expansion in order to obtain tumour-reactive T-lymphocytes.

In Vitro Expansion

The in vitro expansion step iv) of the method according to the invention comprises i) a first phase of stimulating tumour-reactive CD4+ helper and/or CD8+ T-lymphocytes with tumour-derived antigen together with at least one substance having agonistic activity towards the IL-2 receptor, to promote survival of tumour-reactive CD4+ helper and/or CD8+ T-lymphocytes, and ii) a second phase of activating and promoting growth of tumour-reactive CD4+ helper and/or CD8+ T-lymphocytes, wherein the second phase ii) is initiated when the CD25 cell surface marker (IL-2R marker) is down-regulated on T-lymphocytes.

Phase i)

The purpose of the first phase i) is to obtain a culture comprising a substantially high ratio of tumour-reactive CD4+ helper and/or CD8+ T-lymphocytes. The first phase is to be considered a "nursing phase" where the tumour-reactive T-lymphocytes are brought to survive and divide. Depending on the source of the T-lymphocytes (starting material for the in vitro expansion method), they may have phased relatively harsh conditions, such as, e.g., suppression and inhibition by factors secreted by cancer cells.

The starting material for use in the expansion method according to the invention may be a mixture of lymphocytes obtained from lymph nodes draining a primary tumour and/or a metastasis, such as, e.g., a sentinel or metinel lymph node. These can be identified during surgery e.g. by injection of a lymph node locator, such as, e.g., a tracer substance, around or into the tumour or metastasis. The lymph node locator, such as, e.g., the tracer is transported in the lymph capillaries and accumulates in the sentinel/metinel node(s), thus identifying the tumour or metastasis draining lymph node(s). The inventors have recently shown that the first lymph nodes to receive drainage from a tumour are a potential rich source for naturally tumour-reactive CD4+ helper and/or CD8+ T-lymphocytes for in vitro expansion, as such nodes may contain a substantial amount of T-lymphocytes, that have been sensitized towards tumour-antigens and undergone in vivo expansion in the lymph nodes.

An alternative source of CD4+ helper and/or CD8+ T-lymphocytes may be the blood of a subject suffering from cancer, such as, e.g., peripheral blood. The subject may be an untreated patient that has had the disease for a long time or an already treated patient, wherefrom peripheral T-lymphocytes sensitized towards a tumour may be obtained. Other suitable sources of CD4+ helper and/or CD8+ T-lymphocytes include bone marrow, spleen tissue and tumours.

However, in a preferred embodiment of the invention, the starting material is obtained from sentinel or metinel lymph nodes.

The T-lymphocytes to be expanded in culture can be obtained from the subject to be treated, i.e. the resulting specific tumour-reactive T-lymphocytes for administering may be autologous. However, the T-lymphocytes can also be obtained from a source other than the subject to be treated, such as, e.g. another subject suffering from a cancer. In such case the recipient and the expanded tumour-reactive T-lymphocytes are preferably immunologically compatible (or the recipient is otherwise made immuno-tolerant of the expanded tumour-reactive T-lymphocytes).

Depending on the source of the starting material, it will comprise a mixture of various lymphocytes, such as, e.g., T-lymphocytes, B-lymphocytes, antigen presenting cells, tumour-reactive T-lymphocytes and non-activated/non-reactive T-lymphocytes. In order to promote survival specifically of the tumour-reactive CD4+ helper and CD8+ T-lymphocytes, tumour-derived antigen and one or more substances having agonistic activity towards the IL-2 receptor are added.

As mentioned above the first phase i) is initiated by adding at least one substance having agonistic activity towards the IL-2 receptor. The function of such substances is to stimulate T-lymphocytes via the IL-2 receptor to promote cell division of T-lymphocytes, thereby preventing cell death.

Antigen specific MHC restricted activation of T-lymphocytes promotes clonal expansion of the useful T-lymphocyte population specific for the recognition of tumour cells. On the contrary, unspecific activation of T lymphocytes will lead to the expansion of T lymphocyte clones recognizing irrelevant peptides without any relation to the recognition of tumour cells, thus the majority of unspecifically expanded T lymphocytes will not recognize the tumour.

The invention aims to promote specific activation and growth of tumour-reactive CD4+ helper and CD8+ T-lymphocytes. A specific activation against a certain tumour antigen enables the T-lymphocytes to have therapeutic effect when administered to a cancer patient with the same tumour type as the T-lymphocytes are activated against.

Administration of unspecifically activated T-lymphocytes would have no or a very low probability of having therapeutic effect against any cancer, due to the small number of tumour relevant T lymphocytes.

In one embodiment of the invention the substances having agonistic activity towards the IL-2 receptor are agonists. Examples of such substances include proteins, polypeptides, peptides, antibodies, affibodies, and fragments thereof, fusion proteins, synthetic and/or organic molecules, such as, e.g., small molecules, and natural ligands. In a preferred embodiment the substance is the natural ligand of the IL-2 receptor, namely IL-2.

If IL-2 is used it is preferentially added in a low dose in order to reduce lymphocyte apoptosis and to increase the population of CD4 positive helper tumour-reactive T-lymphocytes. In a specific embodiment of the invention, the low dose of IL-2 is from about 100 IU/ml culture medium to about 700 IU/ml culture medium, such as, e.g., from about 100 IU/ml culture medium to about 600 IU/ml culture medium, from about 100 IU/ml culture medium to about 500 IU/ml culture medium, from about 100 IU/ml culture medium to about 400 IU/ml culture medium, from about 100 IU/ml culture medium to about 300 IU/ml culture medium and from about 100 IU/ml culture medium to about 200 IU/ml culture medium. In a specific embodiment, the amount of IL-2 added is 240 IU/ml.

In case other substances, than IL-2, having agonistic activity towards the IL-2 receptor are used the specific doses of these should be such that lead to an effect corresponding to the effect obtained by the above-mentioned doses of IL-2.

A further amount of the at least one substance having agonistic activity towards the IL-2 receptor may be added regularly throughout phase i), such as, e.g., every $2^{nd}$, $3^{rd}$ or $4^{th}$ day of phase i), in order to maintain optimal conditions for promoting cell division. By the term every $2^{nd}$, $3^{rd}$ or $4^{th}$ is intended to mean that at least one substance having agonistic activity towards the IL-2 receptor is added throughout phase i) every $2^{nd}$, $3^{rd}$ or $4^{th}$ day, starting at the $2^{nd}$, $3^{rd}$ or $4^{th}$ day after the first addition of the at least one substances having agonistic activity towards the IL-2 receptor, i.e. after initiating phase i).

In one embodiment the substance to be added regularly throughout phase i) is an agonist of IL-2. In a preferred embodiment the substance is IL-2.

The further dose of substances having agonistic activity towards the IL-2 receptor, such as, e.g., IL-2, to be added regularly, such as, e.g. every $2^{nd}$, $3^{rd}$, or $4^{th}$ day lies within the ranges mentioned above.

A further important step in the first phase i) of expansion is the addition of tumour-derived antigen in order to promote cell division of T-lymphocytes expressing T lymphocyte receptors recognizing tumour antigens, i.e. tumour-reactive T-lymphocytes.

The optimal point of time to add the tumour-antigen is depending on the source of lymphocytes. When the lymphocytes originates from lymph nodes, such as, e.g., sentinel lymph nodes, or from tumours, the lymphocytes may have been subjected to close proximity and immuno-suppression by tumour cells, and need incubation with a substance having agonistic activity towards the IL-2 receptor, such as, e.g., IL-2 for some days in order to promote the ability of the T-lymphocytes to respond with proliferation upon tumour antigen presentation. Accordingly, in such case the tumour-derived antigen is preferentially added from day 2 to and including day 5 of the first phase i), such as, e.g., on day 2, on day 3, on day 4 or on day 5.

If the lymphocytes originate from blood, the tumour-derived antigen may be added already when the first phase i) is initiated, i.e. together with the substance having agonistic activity towards the IL-2 receptor, as the T-lymphocytes have not been subjected to the above-mentioned immuno-suppression by tumour cells. Accordingly, when blood is used, the tumour-derived antigen is added essentially at the same time as when phase i) is initiated or at the most up to 2 days thereafter.

The tumour-derived antigen, such as, e.g., a tumour homogenate, is likely to be endocytosed and processed by antigen presenting cells present in the starting material, such as, e.g., B-lymphocytes, dendritic cells and macrophages. In most cases the tumour-derived antigen will be presented by class II MCH molecules leading to cell division of $CD4^+$ helper tumour-reactive T-lymphocytes. However, by cross presentation antigens taken up by endocytosis may be processed and presented in the class I pocket resulting in activation of $CD8^+$ T lymphocytes. As stated above, one of the objects of the expansion method is to in some respect imitate the natural pathway of the patients own immune system, and to a certain degree let the components of the patients immune system determine whether $CD4^+$ or $CD8^+$ lymphocytes are generated, depending on whether antigen is presented by MCHI or MCHII. In most cases, the antigens will be presented by the class II MCH molecule leading to generation of $CD4^+$ T-lymphocytes, however, in some cases $CD8^+$ T-lymphocytes are generated.

In a specific aspect of the invention, at the end of phase i) the sum of $CD4^+$ and $CD8^+$ T-lymphocytes isolated from a small intestine cancer comprise at least 70% of the cell population, such as at least 75%, at least 80%, at least 85%, at least 90%, at least 95% or 100%. In another specific aspect of the invention, at the end of phase i) $CD4^+$ T-lymphocytes isolated from a small intestine cancer comprise at least 50% of the cell population, such as at least 60%, at least 70%, at least 75%, at least 80%, at least 85%, at least 90%, or at least 95%. In yet another specific aspect of the invention, at the end of phase i) CD8+ T-lymphocytes isolated from a small intestine cancer comprise at least 1% of the cell population, such as at least 5%, at least 10%, at least 15%, at least 20%, or at least 25%. In a further specific aspect of the invention, at the end of phase i) the number of CD4+ and/or CD8+ T-lymphocytes isolated from a small intestine cancer has increased by a factor 1.5, such as 2, 3, 4, 6, 8, 10, 12, 14, 16, 18, or 20. In another further specific aspect of the invention, at the end of phase i) the ratio of CD4+ to CD8+ T-lymphocytes isolated from a small intestine cancer has increased by a factor 1, such as 1.25, 1.5, 1.75, 2, 3, or 4 as compared to the beginning of the expansion.

In a specific aspect of the invention, at the end of phase i) the sum of CD4+ and CD8+ T-lymphocytes isolated from a gallbladder cancer comprise at least 70% of the cell population, such as at least 75%, at least 80%, at least 85%, at least 90%, at least 95% or 100%. In another specific aspect of the invention, at the end of phase ii) CD4+ T-lymphocytes isolated from a gallbladder cancer comprise at least 70% of the cell population, such as at least 75%, at least 80%, at least 85%, at least 90%, or at least 95%. In yet another specific aspect of the invention, at the end of phase ii) CD8+ T-lymphocytes isolated from a gallbladder cancer comprise at least 1% of the cell population, such as at least 5%, at least 10%, at least 15%, at least 20%, or at least 25%.

Phase ii)

The purpose of the second phase ii) is to activate and expand the tumour-reactive CD4+ helper and/or CD8+ T-lymphocytes obtained by phase i) and to obtain a specific sub-population of tumour-reactive CD4+ helper and/or CD8+ T-lymphocytes by directing them into a desired pathway.

The present inventors have found, that one way of determining the optimal point in time to initiate phase ii) is by monitoring the expression of the CD25 cell surface marker on the T-lymphocytes, in order to determine specifically when the T-lymphocytes are susceptible to re-stimulation. The present inventors have found that the second phase ii) should preferably be initiated when the expression of CD25 on T-lymphocytes is down-regulated. CD25 is an activation marker, indicating that the lymphocytes have received an activating signal. If the second phase is initiated when the expression of CD25 on the T-lymphocytes is high, meaning that the lymphocytes have already received a signal, cell death would occur.

The down-regulation of CD25 is defined as that a substantial part of the T-lymphocyte population express very few or essentially none CD25 markers. In a preferred embodiment the down-regulation of CD25 is defined as that less than 5% of the T-lymphocyte population expresses CD25, i.e. 95% or more of the T-lymphocytes in the culture do not express CD25 at all. The 5% or less of the T-lymphocytes expressing CD25 are most likely regulatory CD4+ T-lymphocytes, which have a high permanent expression of CD25. In addition, the T-lymphocyte population should preferably express very few or essentially none Foxp3 markers, which are specific markers of regulatory T-lymphocytes. In a preferred embodiment the down-regulation of Foxp3 is defined as that less than 5% of the T-lymphocyte population expresses Foxp3, i.e. 95% or more of the T-lymphocytes in the culture do not express Foxp3 at all.

Besides CD25, there are also other markers, the expression of which is relevant to monitor in order to determine the optimal point in time to initiate the second phase. Examples of such markers are the early activation marker CD69, and MCHII, which is an activation marker for T-lymphocytes. As the expression of CD69 and MCHII indicates that the "activation program" of the T-lymphocytes is already turned on, meaning that the cells are not able to respond to additional stimuli, both of these markers should preferably be down-regulated before the second phase is initiated. The term down regulation may be defined as that less than 5-10% of the T-lymphocyte population expresses CD69 and/or MCHII.

In another embodiment of the present invention, anti-CD4 antibodies are used to separate T helper cells from possible tumour cells in the culture in the expansion in phase ii) of the expansion method.

In a further or yet another embodiment of the present invention, products such as Dynabeads® with anti-CD3 and anti-CD28 antibodies are used to promote the expansion in phase ii) of the expansion method. Use of Dynabeads® CD3/CD28 will provide lymphocytes with activation signals and could also be used for separation from possible tumour cells in the culture. Dynabeads® CD3/CD28 will bind to T lymphocytes expanded antigen specifically during phase i), where these cells now can be enriched magnetically. Since the initial antigen specific activation has initiated and led to clonal T lymphocyte expansion the Dynabeads® CD3/CD28 restimulation will further promote clonal expansion since phase i) does not support activation of unspecific T lymphocyte clones.

Even though the exact starting point of phase ii) will vary depending on when the lymphocytes has acquired the preferred expression of specific markers, the second phase ii) is most often initiated from day 17 to and including day 23 of the first phase i), such as, e.g. on day 17, on day 18, on day 19, on day 20, on day 21, on day 22 or on day 23. In other words, the point in time, where the lymphocytes expresses the preferred amount and combination of markers, is most often seen as being from day 17 to day 23 of the first phase i).

The expansion of the T-lymphocytes, i.e. phase i) and ii) will most often take place in a suitable culture medium. Preferably a serum-free medium or autologous serum is used in order to avoid the risk of transmitting diseases to the patient. Examples of suitable standard media include AIMV medium, RPMI 1640, DMEM and MEM. However, other media may also be used, comprising a suitable blend of amino acids, steroids, vitamins, growth factors, cytokines and minerals.

During the two phases of the expansion, the cells may be split into several culture vessels in order to maintain a suitable cell density in the cultures. The density of the T-lymphocytes in the expansion phases should preferably be from about 3 to about 6 million cells/ml of culture medium.

During expansion an exchange of culture medium with fresh medium, a step, which is denominated conditioning of the medium, may also be needed. The point of time to split cultures and to condition the medium may be determined based on the morphology of the cells and the cell culture density (which should not exceed about 6 million cells/ml), or the medium may contain a suitable indicator, such as, e.g., a phenol indicator. In case an indicator is included in the medium, the point of time to split cultures or condition medium may be based on the color of the medium. If a phenol red indicator is used, the cells should be split or conditioned, when the medium turns yellow, indicating that the pH of the culture is turning acidic. A suitable schedule for conditioning the medium used in the present invention may be to exchange from ¼ to ½, such as, e.g., ⅓ of the medium every 3-9 days, such as, e.g. once a week.

Except for the specific conditions mentioned herein, for other parameters standard conditions for growth of lymphocyte cultures will be used, such as, e.g. a temperature of 37° C. and 5% $CO_2$.

As mentioned above, the second phase ii) is initiated by the addition of tumour-derived antigen as defined above to the T-lymphocytes for activating the tumour-reactive CD25-negative T-lymphocytes, in order to promote clonal expansion of tumour-reactive T-lymphocytes.

In a specific embodiment of the invention antigen presenting cells (APCs) are added to the T-lymphocytes together with the tumour-derived antigen. Antigen presenting cells (APCs) include leukocytes such as, e.g., monocytes, macrophages and lymphocytes, such as, e.g., B cells. These diverse cell types have in common the ability to present antigen in a form that is recognized by specific T lymphocyte receptors. The leukocyte preparation is isolated from, for example, blood, lymph fluid, bone marrow, lymphatic organ tissue or tissue culture fluid obtained from the patient to be treated. In a preferred embodiment the APCs cells are irradiated peripheral blood leucocytes containing antigen-presenting B-cells and/or monocytes. The amount of APCs added lies within the range of from about 0.5 million APCs/ml lymphocyte culture to about 5 million APC/ml lymphocyte culture, such as, e.g., from about 1 million APCs/ml lymphocyte culture to about 4 million APC/ml lymphocyte culture, from about 1 million APCs/ml lymphocyte culture to about 3 million APC/ml lymphocyte culture, or from about 1 million APCs/ml lymphocyte culture to about 2 million APC/ml lymphocyte culture.

Besides the addition of tumour-derived antigen to the T-lymphocytes in order to promote clonal expansion of tumour-reactive T-lymphocytes, the second phase ii) comprises the addition of specific components the function of which are to direct the expansion of the tumour-reactive T-lymphocytes towards the desired sub-population.

As mentioned above, the present invention provides a method for the generation of tumour-reactive CD4+ helper T-lymphocytes. CD4+ helper T-lymphocytes recognizes and binds tumour antigen when the antigen is associated with a major histocompatibility complex class II molecule. Activated CD4+ helper T lymphocytes secrete cytokines, proteins and/or peptides that stimulate other cells of the immune system, such as other lymphocytes. The most common cytokine secreted is interleukin-2 (IL-2), which is a potent T lymphocyte growth factor. Activated, proliferating CD4+ helper T-lymphocytes can differentiate into two major subtypes of cells, Th1 and Th2 cells, which are defined on the basis of specific cytokines produced. Th1 cells produce interferon-gamma and interleukin 12 (IL-12), while Th2 cells produce interleukin-4, interleukin-5 and interleukin-13. Th1 T-lymphocytes are believed to promote activation of cytotoxic T lymphocytes (Tc), NK cells, macrophages, and monocytes, all of which can attack cancer cells and generally defend against tumours.

T-helper (CD4+) lymphocytes of type Th1 and Th2 can differentiate into memory cells and effector cells. Memory T-helper (CD4+) lymphocytes are specific to the antigen they first encountered and can be called upon during a secondary immune response, calling forth a more rapid and larger response to the tumour-antigens. There is evidence in humans that lymphocytes survive at least 20 years; perhaps for life. Effector CD4+ T-lymphocytes are active cells producing cytokines and INF-gamma. For an effective treatment of cancer, administration of tumour-reactive T-lymphocytes of the Th1 type is especially beneficial, as this type is believed to promote activation of cytotoxic T lymphocytes (Tc), NK cells, macrophages, and monocytes, all of which can attack cancer cells and generally defend against tumours. I.e. in a specific embodiment the invention relates to a method for generating tumour-reactive CD4+ helper T-lymphocytes, and in a further embodiment, the percentage of T-lymphocytes of the Th2 type generated by the present method is 30% or less, such as, e.g., 25% or less, 20% or less, 15% or less, 10% or less, 5% or less or 0%, i.e. at least 70% of the tumour-reactive CD4+ T-lymphocytes are of the Th1 type, such as, e.g. at least 75%, at least 80%, at least 85%, at least 90%, at least 95% or 100%.

Accordingly, the second phase may comprise the addition of a substance capable of up-regulating IL-12R on the T-lymphocytes. Up regulation of the IL-12R will increase the readiness of the T cell to receive and optimize the IL-12 cytokine activation resulting in maximal STAT-4 signalling and thus skewing the lymphocytes towards Th1 cells and IFN-γ production.

The substance(s) capable of up-regulating IL-12R on the T-lymphocytes may be substance(s) having agonistic activity towards an interferon receptor. In one embodiment of the invention the substances having agonistic activity towards the interferon receptor are agonists. Examples of such substances include proteins, polypeptides, peptides, antibodies, affibodies, and fragments thereof, fusion proteins, synthetic and/or organic molecules, such as, e.g., small molecules, and natural ligands. In a specific embodiment the substance is the natural ligand of the interferon receptor, namely an interferon, such as interferon-α.

The optimal point of time to add the substance(s) capable of up-regulating IL-12R on the T-lymphocytes, such as, e.g. a substance having agonistic activity towards an interferon receptor may be determined by measuring the level of IL-12 in the culture medium. The substance(s) should preferably be added when the level of IL-12 is at least 1 fold, such as, e.g., at least 2, at least 3 fold, at least 4 fold, or at least 5 fold increased as compared to the level of IL-12 on day 1 of phase ii). In most cases, such an increase in the level of IL-12 will be seen from day 2 to and including day 4 after initiating the second phase ii), such as, e.g. on day 2, on day 3 or on day 4.

In order to substantially avoid the generation of tumour-reactive T-lymphocytes of the Th2 type, the second phase may further comprise the addition of one or more substances capable of antagonizing development of Th2 type T-lymphocytes. Examples of such substances are substances capable of neutralizing the interleukins IL-4, IL-5, IL-10, and/or TGF-beta (the latter not being an interleukin) all four of which are required for the establishment of the Th2 cytokine profile and for down regulation of Th1 cytokine production.

Examples of such substances include proteins, polypeptides, peptides, soluble receptors, antibodies, affibodies, and fragments thereof, fusion proteins, synthetic and/or organic molecules, such as, e.g., small molecules, and natural ligands. In a specific embodiment the substances are selected from antibodies that binds to the interleukins, thereby neutralizing them, such as, e.g. anti IL-4 antibody, anti IL-5 antibody and/or anti IL-10 antibody, together with soluble receptors (such as, e.g. TGF-beta receptor I and II) and binding proteins for TGF-beta (such as, e.g. LAP and/or LTBP).

The one or more substances capable of antagonizing development of Th2 type T-lymphocytes, such as, e.g., one or more substances capable of neutralizing IL-4, IL-5, IL-10 and/or TGF-beta may be added on day 1 of the second phase ii). However, as antibodies are expensive, the addition of antibodies can also be performed in a subsequent step after addition of the substance capable of up-regulating IL-12R on the T-lymphocytes, such as, e.g., one day, two days or three days after addition of the substance capable of up-regulating IL-12R on the T-lymphocytes.

The neutralizing substances should be added in an amount sufficient to neutralize the interleukins, such as, e.g., in a 10-100 fold (molar) excess of the amount of interleukin to be neutralized. When using antibodies, a final concentration of from about 2 to about 4 ng/ml culture medium will normally be needed. For other types of neutralizing substances, a final concentration, giving the same effect as the concentration mentioned for antibodies, should be used.

In order to maintain the suppression of the development of Th2 type T-lymphocytes a further amount of the one or more substance capable of antagonizing development of Th2 type T-lymphocytes, such as, e.g., one or more substance capable of neutralizing IL-4, IL-5, IL-10 and/or TGF-beta may be added regularly throughout phase ii), such as, e.g. every $2^{nd}$, $3^{rd}$ or $4^{th}$ day of phase ii). It is to be understood that by the term every $2^{nd}$, $3^{rd}$ or $4^{th}$ is intended to mean that at least one substance capable of antagonizing development of Th2 type T-lymphocytes is added throughout phase i) every $2^{nd}$, $3^{rd}$ or $4^{th}$ day, starting at the $2^{nd}$, $3^{rd}$ or $4^{th}$ day after the first addition of the at least one substance capable of antagonizing development of Th2 type T-lymphocytes.

Furthermore, as for phase i) a further amount of a substance having agonistic activity towards the IL-2 receptor, such as, e.g., an agonist may be added regularly throughout phase ii) such as, e.g., every $2^{nd}$ to $4^{th}$ day of phase ii), i.e. on the $2^{nd}$, $3^{rd}$ or $4^{th}$ day in order to maintain optimal conditions promoting cell division. The dose of the substance to be added regularly lies within the optimal ranges mentioned under phase i) for addition of substances having agonistic activity towards the IL-2 receptor, such as, e.g., IL-2.

In order to favor the generation of Th1 type tumour-reactive T-lymphocytes, the second phase ii) may comprise adding one or more substances promoting the development of Th1 type T-lymphocytes. Examples of such substances are substances having agonistic activity towards the IL-7, IL-12, IL-15 and/or IL-21 receptor. More specific, the substances may be agonists for the IL-7, IL-12, IL-15 and/or IL-21 receptor. Examples of such agonists include proteins, polypeptides, peptides, antibodies, affibodies, and fragments thereof, fusion proteins, synthetic and/or organic molecules, such as, e.g., small molecules, and natural ligands. In a specific embodiment the substances are the natural ligands of the IL-7, IL-12, IL-15 and/or IL-21 receptor, respectively, such as IL-7, IL-12, IL-15 and/or IL-21.

The effect of IL-12 is activating the IFN-gamma inducing STAT pathway by stimulating the IL-12R thereby promoting activation of Th1 lymphocytes. The function of IL-21 is to enhance proliferation, activation and development towards a Th1 type of T-lymphocytes.

Both IL-7 and IL-15 work by promoting homeostatic expansion of the T-lymphocytes, enhancing the enumeration of activated Th1 programmed T-lymphocytes.

The optimal point of time to add one or more substances promoting development of Th1 type T-lymphocytes is when the T-lymphocytes are susceptible to modification. If the substances are added when the T-lymphocytes are not susceptible to modification, the addition will have no effect, i.e. the development of Th1 type T-lymphocytes will not be favoured. In order to determine the optimal point in time for adding substances promoting development of Th1 type T-lymphocytes, such as, e.g., substances having agonistic activity towards the IL-7, IL-12, IL-15 and/or IL-21 receptor, the production of INF-γ by the T-lymphocytes, may be monitored. In a preferred embodiment, the one or more substances promoting the development of Th1 type T-lymphocytes, such as, e.g., substances having agonistic activity towards the IL-7, IL-12, IL-15 and/or IL-21 receptor should be added when the level of IFN-gamma is increased as compared to the level of IFN-gamma on initiation of second phase ii).

In a specific embodiment, the increase in IFN-gamma level may be determined as at least a 1 fold increase in IFN-gamma level, such as, e.g., at least a 2 fold, at least a 3 fold, at least a 4 fold increase as compared to the level of IFN-gamma on initiation of the second phase ii). Often will such an increase can be correlated to that the content IFN-gamma in the culture medium should be at least 100 picogram/ml culture medium, such as, e.g. at least 150 picogram/ml culture medium, at least 200 picogram/ml culture medium or at least 250 picogram/ml culture medium.

When determining the optimal point in time to add substances promoting development of Th1 type T-lymphocytes, such as, e.g., substances having agonistic activity towards the IL-7, IL-12, IL-15 and/or IL-21 receptor, one may further look at the expression of the activation markers CD25 and CD69 on CD4+ T-lymphocytes, which markers should preferentially be up-regulated. By up-regulation is understood that at least about 40% to about 60% or more of the CD4+ T-lymphocytes should express CD25 and CD69 as compared to the expression of CD25 and CD69 on T-lymphocytes on day 1 of phase ii), showing that the T-lymphocytes have received an activating signal.

Normally the optimal point of time for adding the substances promoting development of Th1 type T-lymphocytes will fall subsequent to the steps of adding the substances capable of up-regulating IL-12R on the T-lymphocytes and the substances capable of antagonizing development of Th2 type T-lymphocytes. More specific the optimal point in time to add the substances promoting development of Th1 type T-lymphocytes will fall between day 5 to day 8 after initiating the second phase ii), such as, on day 5, day 6, day 7 or day 8.

In case IL-7, IL-12, IL-15 and/or IL-21 are added the concentration of each of these substances in the culture medium should lie within the range from about 150 IU/ml culture medium to about 300 IU/ml culture medium, such as, e.g. 250 IU/ml culture medium. When other substances than the specific ones mentioned is used, they should be added to the culture in final concentration, which leads to the same effect as the addition of IL-7, IL-12, IL-15 and/or IL-21 within the specific ranges mentioned will give.

As mentioned above, the present method is preferentially used for the expansion of T-lymphocytes in order to achieve CD4+ tumour-reactive T-lymphocytes of the Th1 type. One further aspect of the invention is that by using the method described herein for expanding tumour-reactive T-lymphocytes, a relatively high amount of T-lymphocytes of the memory type will be obtained. In treating cancer it is of course important that the patient to be treated receive a high amount of effector tumour-reactive CD4+ T-lymphocytes, as these—as mentioned above—promote activation of cytotoxic T lymphocytes (Tc), NK cells, macrophages, and monocytes, all of which can attack cancer cells and generally defend against tumours.

However, by at the same time administering a substantial amount of memory tumour-reactive CD4+ T-lymphocytes, the patient achieve up to life long protection towards recurrence of the tumour or metastasis of the primary tumour.

Accordingly, the present invention relates to a method for the preparation of memory T-lymphocytes. Normally, when a culture of tumour-reactive T-lymphocytes are expanded according to the present invention from about 35% to about 90% of tumour-reactive T-lymphocytes of the memory type, such as, e.g. from about 40% to about 90%, from about 50% to about 80% or from about 60% to about 70%, will be obtained. The present inventors speculates that the fact that the lymphocytes in phase i) are allowed to regenerated before tumour antigen is added, together with the relatively slow expansion phase leads to formation of a high ratio of memory lymphocytes to effector lymphocytes.

As mentioned above the expression of the cell surface activation markers CD25 and CD69 on the T-lymphocytes may be used for determining when to initiate important steps of the present method, such as, e.g., when to initiate the second phase ii). Accoridngly, it may be beneficial to continuously monitor the expression of CD25 and CD69 throughout phase i) and phase ii), such as, e.g., every $2^{nd}$, every $3^{rd}$ or every $4^{th}$ day.

As one of the purposes of the present method is to obtain a high number of specific CD4+ tumour-reactive T-lymphocytes, which may be used for administering to a patient, the tumour-reactive T-lymphocytes may be harvested at some point, leading to the termination of the expansion step. The optimal point of time to harvest the tumour-reactive T-lymphocytes is when the expression of CD25 on the T-lymphocytes is down-regulated, where the down-regulation is defined as that 5% or less of the CD4+ T-lymphocyte population expresses CD25. The optimal point in time to harvest may also be determined based on measurement of the amount of IFN-gamma produced. The IFN-gamma production should be at least 2 fold increased, such as, e.g., at least 3 fold, at least 4 fold or at lest 5 fold increased as compared to initial IFN-gamma production, which normally correspond to a level of IFN-gamma of at least 100 pg/ml of culture medium.

Normally, this event will occur from day 10 to and including day 14 after initiating the second phase ii), i.e. normally the cells will be harvested from day 10 to and including day 14 after initiating the second phase ii).

Accordingly, the entire process for expansion of tumour-reactive T-lymphocytes according to the invention may in general take from about 25 days to and including about 45 days, such as, e.g. from about 26 days to and including about 44 days, from about 27 days to and including 43 days, from about 27 days, to and including 42 days, from about 27 days to and including 41 days, and from about 27 days to and including about 40 days.

Instead of harvesting the tumour-reactive T-lymphocytes when the CD25 marker is down regulated, they may be subjected to one or more additional rounds of phase ii). This could be beneficial to do if the amount of tumour-reactive T-lymphocytes obtained by the expression method is not considered an effective amount to be administered to a patient suffering from cancer, or if the patient is in a chemo-therapy treatment regimen, where it may be considered beneficial to postpone the administration of T-lymphocytes until the chemo-therapy treatment is finished. In order to determine whether the tumour-reactive T-lymphocytes should be subjected to one or more additional rounds of phase ii) one may look at the level of IFN-gamma produced, and/or the total number of tumour-reactive T-lymphocytes obtained and/or the expression of CD25. In the case the IFN-γ levels is 30 pg/ml culture medium or less, such as, e.g. 20 pg/ml culture medium or less, and/or the total number of T cells are unsatisfactory, additional rounds of phase ii) may be initiated beginning when the majority of T cells are CD25 negative (i.e. less than 5% of the T-lymphocytes population express CD25) and thereby susceptible to restimulation.

After harvest the tumour-reactive T-lymphocytes may be purified by any conventional means, such as, e.g. by using density gradient, such as, e.g., a Ficoll medium. A portion of the tumour-reactive T-lymphocytes may be stored by freezing in a suitable freezing medium after harvesting and purifying the tumour-reactive T-lymphocytes.

In a specific aspect of the invention, at the end of phase ii) the sum of CD4+ and CD8+ T-lymphocytes isolated from a small intestine cancer comprise at least 70% of the cell population, such as at least 75%, at least 80%, at least 85%, at least 90%, at least 95% or 100%. In another specific aspect of the invention, at the end of phase ii) CD4+ T-lymphocytes isolated from a small intestine cancer comprise at least 50% of the cell population, such as at least 60%, at least 70%, at least 80%, at least 90%, or at least 95%. In yet another specific aspect of the invention, at the end of phase ii) CD8+ T-lymphocytes isolated from a small intestine cancer comprise at least 5% of the cell population, such as at least 10%, at least 15%, at least 20%, at least 25%, at least 30%, or at least 35%.

In a specific aspect of the invention, at the end of phase ii) the sum of CD4+ and CD8+ T-lymphocytes isolated from a mesothelioma comprise at least 70% of the cell population, such as at least 75%, at least 80%, at least 85%, at least 90%, at least 95% or 100%. In another specific aspect of the invention, at the end of phase ii) CD4+ T-lymphocytes isolated from a mesothelioma comprise at least 50% of the cell population, such as at least 60%, at least 70%, at least 80%, at least 90%, or at least 95%. In yet another specific aspect of the invention, at the end of phase ii) CD8+ T-lymphocytes isolated from a mesothelioma comprise at least 5% of the cell population, such as at least 10%, at least 15%, at least 20%, at least 25%, at least 30%, at least 35%, or at least 35%.

Method of Treatment

The tumour-reactive T-lymphocytes obtained by an improved expansion method as described above may be used in a method for treating a subject suffering from a disease of neoplastic origin or for effecting tumour regression in a subject having a tumour, the method comprising administering to the subject in need thereof an effective amount of tumour-reactive T-lymphocytes according to the invention.

The method described herein may be used for treatment of any solid neoplasm of epithelial, mesenchymal or embryological origin in any anatomical location, such as e.g., for epethilal neoplasms e.g. carcinomas in the breast, colon, pancreas, bladder, small intestines, prostate, cervix, vulva, ovaries; for mesenchymal neoplasms e.g. sarcomas in the joints, bones, muscles and tendons and some haematological such as lymphomas; for embryological neoplasms, e.g. teratomas.

In a specific embodiment the present invention provides a method for use for the treatment of a neoplastic disease selected from gall bladder cancer, hepato cellular cancer, ovarian cancer, small intestine cancer, lung cancer, mesothelioma, breast cancer, kidney cancer, pancreas cancer, prostate cancer, carcinoid cancer, leiomyosarcoma, or metastasis thereof.

The tumour-reactive T-lymphocytes obtained by an improved expansion method are used herein for treating patients suffering from a gall bladder cancer, hepato cellular cancer, ovarian cancer, small intestine cancer, lung cancer, mesothelioma, breast cancer, kidney cancer, pancreas cancer, prostate cancer, carcinoid cancer, leiomyosarcoma, or metastasis thereof.

The definition of an effective amount of tumour-reactive T-lymphocytes is depending on the specific type of lymphocytes, the ratio of memory to effector T-lymphocytes and on the severity of the disease. However, in average a minimum of at least 10 million, such as, e.g. at least 20 million, at least 30 million, at least 40 million, at least 50 million, at least 60 million, at least 70 million or at least 80 million tumour-reactive T-lymphocytes may be administered. The present inventors have not identified any upper limit with respect to the amount of tumour-reactive T-lymphocytes to be administered in a single dose.

In a preferred embodiment the tumour-reactive T-lymphocytes for administration comprises a combination of effector T-lymphocytes and memory T-lymphocytes. More specific the amount of tumour-reactive T-lymphocytes of the memory type may be from about 35% to about 90%, such as, e.g. from about 40% to about 90%, from about 50% to about 80% or from about 60% to about 70%, and a percentage of effector T-lymphocytes from about 10% to about 65%, such as, e.g., from about 20% to about 50% or from about 30% to about 40%.

The tumour-reactive T-lymphocytes may be formulated as a pharmaceutical composition suitable for parenteral administration to the patient such as, e.g., intravenous, intraarterial, intrathecal, or intraperitonal administration.

When the tumour-reactive T-lymphocytes are administered parenterally, they may be formulated in an isotonic medium, i.e. in a medium having the same tonicity as blood, and comprising one or more substances preventing aggregation of the cells. A specific example of a suitable medium is a 0.9% NaCl solution comprising up to 3% human serum albumin such as, e.g. up to 2% human serum albumin or up to 1% human serum albumin. For intravenously administration the concentration of tumour-reactive T-lymphocytes in the composition to be administered normally lies within the range from about 0.5 million lymphocytes/ml medium to about 4 million lymphocytes/ml medium, such as, e.g., from about 0.5 million lymphocytes/ml medium to about 3 million lymphocytes/ml medium, from about 0.5 million lymphocytes/ml medium to about 2 million lymphocytes/ml medium or from about 1 million lymphocytes/ml medium to about 2 million lymphocytes/ml medium.

The composition comprising tumour-reactive T-lymphocytes may be administered as a single dose or multiple doses. It may be infused over 1 to 2 hours.

The treatment method may be performed once or repeated depending on the severity of the disease. Furthermore, the treatment may be reiterated upon recurrence of the disease.

The treatment according to the present invention may be supplemented with any other relevant treatment for cancer. Such supplemental treatment may be given before, at the same time or after the administration of the lymphocytes and it may be given at frequencies normally used for such treatments. A suitable example of supplemental treatment is chemotherapy and the like.

Kits

The invention further relates to kits for use in a method according to the invention, the kit comprising a medium for cultivation of T-lymphocytes. The medium may be any suitable serum-free medium, such as, e.g., AIMV, RPMI 1640, DMEM or MEM.

The kit may further comprise one or more substances for stimulating, activating and directing tumour-reactive T-lymphocytes. Examples of such substances may be tumour-derived antigen, substances having agonistic activity towards the IL-2 receptor, substances capable of up-regulating IL-12R on the T-lymphocytes, substances capable of antagonizing development of Th2 type T-lymphocytes and/or substances promoting the development of Th1 type T-lymphocytes.

More specific, such substances may be IL-2, interferon-alpha, anti-IL-4 antibody, anti-IL-5 antibody, anti-IL-10 antibody, IL-7, IL-12, IL-15 and/or IL-21.

The kit may also comprise a pharmaceutical composition suitable for intravenous administration. The pharmaceutical composition may be mixed with the population of tumour-reactive T-lymphocytes before administration.

The invention also relates to a kit for identification of sentinel or metinel lymph nodes, the kit comprising one or more syringes and a lymph node locator. In one embodiment, the syringes are prefilled with a lymph node locator.

The kits may also comprise instructions for use, such as, e.g. instructions in the form of computer software.

EXAMPLES

Example 1

Expansion of Tumour-Reactive T-Lymphocytes

Figure 1:
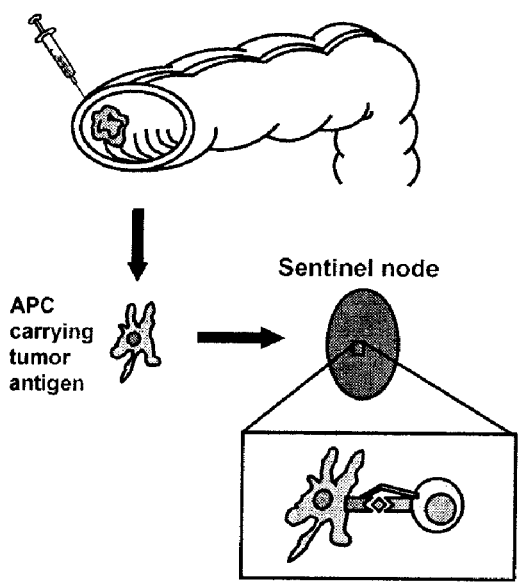
FIG. 1 illustrates that the sentinel node is the natural primary site for the presentation and activation of T cell reactivity towards tumour antigen.

Identification of sentinel nodes was done peroperatively using the sentinel node technique. Briefly, 1 ml of Patent blue dye was injected (Guerbet, Paris) and distributed superficially in the serosa around the tumour. Within five to ten minutes, one to three mesenteric lymph nodes were coloured blue, these sentinel nodes were marked with sutures and removed (see FIG. 1). One non-sentinel mesenteric lymph node, distant from the tumour, was also identified and removed as a control.

The sentinel- and non-sentinel lymph nodes were cut in half and 1 mm thick slices were taken from the center and the periphery. The rest of the lymph nodes were sent for histopathological examination according to routine procedure. A part of the tumour, including a sample of the invasive margin, was also removed for research purposes.

Cell Culture

Phase 1, Initial Activation

The sentinel node material was kept on ice and immediately taken care of using AIM V® Media (Invitrogen) at all times. Single cell suspensions of sentinel node lymphocytes were obtained through gentle homogenisation in a loose fit glass homogenisator, and following homogenisation cells were washed twice in medium. The sentinel node lymphocytes were put in cell culture flasks at 4 million cells/ml and interleukin-2 (IL-2) (Proleukin®, Chiron) was added to a concentration of 240 IU/ml medium.

Autologous tumour extract was prepared by homogenisation with an Ultra Turrax in 5 volumes (w/v) 2×PBS followed by denaturation for 5 minutes at 97° C. Three to four days after initiation of the cell culture autologous tumour extract was added at a concentration of 1/100. For long-term culture the cells were kept in a cell incubator at 37° C. and 5% $CO_2$ and 240 IU IL-2/mL media added every 3-4 days.

Phase II, Activation and Expansion

Figure 2:
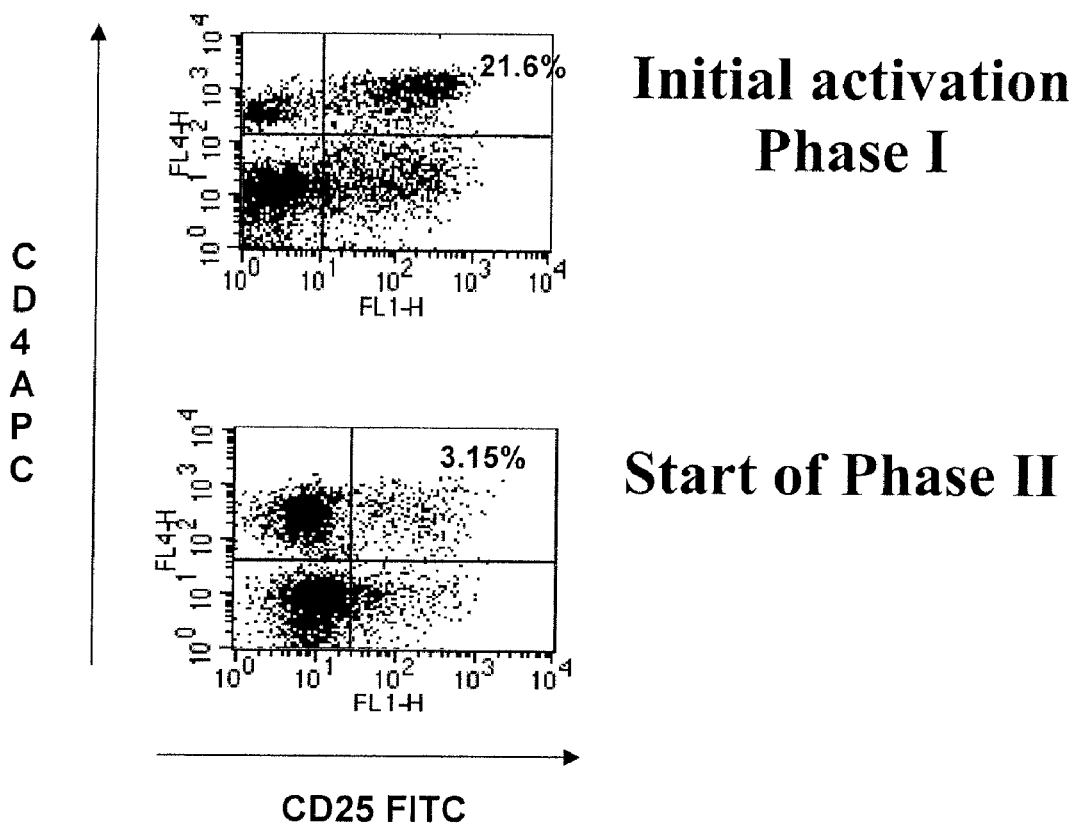
FIG. 2 shows that initially sentinel node lymphocytes are activated with tumour antigen and low dose IL-2 resulting in activation and expression of the activation marker CD25 (Top panel). The end of phase I activation phase is defined by the decreased number of CD4$^+$ T cells expressing CD25 (Bottom panel). When less than 5% of the CD4$^+$ T cells express CD25 phase II is initiated with restimulation with antigen.

After 18-22 days the cell cultures were monitored for the expression of CD25. When the number of CD25 expressing cells was diminished below 5% the cells were restimulated in Phase II (FIG. 2) by the addition of autologus tumour extract at a concentration of 1/100. For efficient antigen presentation autologous PBMC were collected using Ficoll-Paque PLUS (Amersham Biosciences, GE Healthcare), radiated with 2500 rad and added to the cell cultures. Three days after restimulation interferon-α (Introna) in conc. 100-500 IU/ml and anti IL-4 antibody was added to a concentration of 2 μg/ml. After 5 to 8 days IL-12 (4 ng/ml) was added to the expansion in order to promote induction of IFN-γ producing Th1 cells.

The day before transfusion to the patient the cell cultures were subject to purification using a Ficoll-Paque PLUS (Amersham Biosciences, GE Healthcare) in order to retrieve the viable cells in the culture. On the day of transfusion the cells were washed twice in Saline solution (Natriumklorid Baxter Viaflo 9 mg/ml, Baxter) and then transferred to a transfer bag containing 100-200 ml of saline solution and 1% Human Serum Albumin (Baxter). Investigations for microbial presence were performed prior to transfusion. Infusions of the cells were performed during 1-2 hours under professional medical supervision.

Immunological Evaluation

Further immunological evaluation was performed using tritium labelled thymidine incorporation proliferation assays. An aliquot of Sentinel node lymphocytes was set aside for this purpose, a single cell suspension of non-sentinel node lymphocytes was obtained by gentle pressure in a loose fit glass homogenisator and peripheral blood leukocytes were purified by Ficoll-Paque PLUS (Amersham Biosciences, GE Healthcare).

Cells were resuspended and washed twice in RPMI 1640 (Life technologies) containing 2.5% fetal calf serum (FCS) (Life technologies). Finally, cells were resuspended in RPMI 1640 proliferation media containing 10% human AB serum (Sigma), 1% penicillin-streptomycin (Sigma) and 1% glutamine (Sigma). Lymph node cells and purified PBL were used at $3\times10^5$ cells/well in a 96-well plate and stimulated with tumour homogenate diluted 1/100, 1/10 or Con A 10 µg/ml (Sigma) in triplicates. Proliferation was measured on day 5, 6 and 7 by adding 1 µCi of $^3$H-Thymidine/well (Amersham) 18 hours prior to harvesting. Samples were subjected to scintillation counting.

Figure 5:
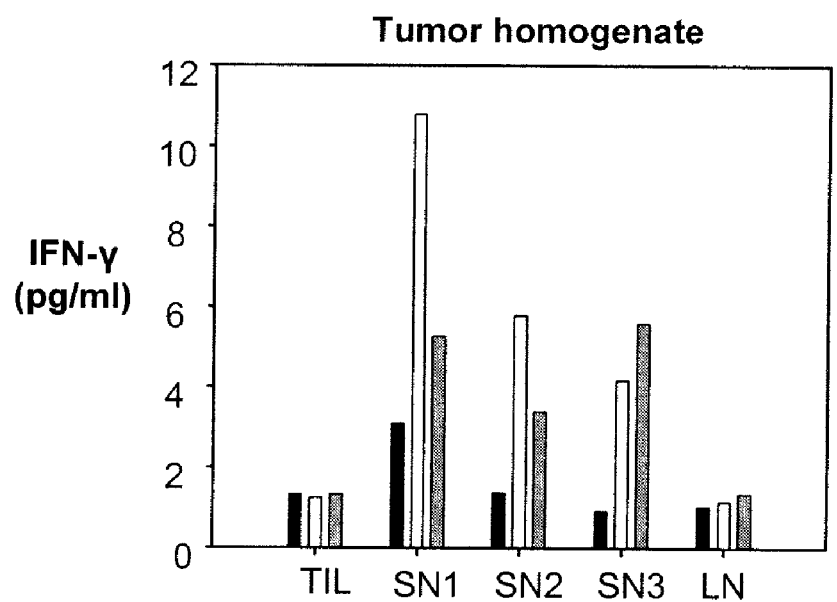
FIG. 5 shows primary cells stimulated in Phase I from the tumour (Tumour infiltrating lymphocytes), sentinel nodes (SN) and an irrelevant lymph node (LN) results in no little IFN-γ production.
Figure 6:
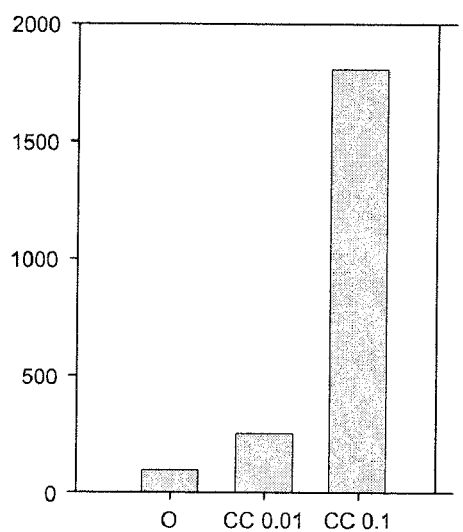
FIG. 6 illustrates that after expansion after phase ii) there is a dose dependent increase in antigen dependent IFN-γ production.
Figure 6:
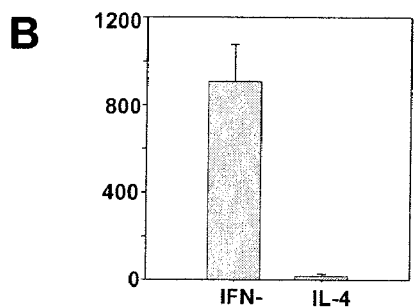

At the start of cell culture, stimulations of lymph node cells and PBL, for the measurement of IFN-γ secretion, were performed in 96-well plates with $3\times10^5$ cells/well in triplicate with tumour homogenate diluted 1/10 and 1/100, or Con A 10 µg/ml (Sigma). The amount of secreted IFN-γ was measured with ELISA (Human IFN-γ Duoset, R&D Systems) on culture supernatants in pooled samples of the triplicates (FIG. 5). At the end of cell cultures samples of the supernatant was removed and IFN-γ and IL-4 secretion measured in triplicates with ELISA (Human IFN—Duoset and Human IL-4 Duoset, R&D Systems) (FIGS. 6 A and 6B).

Flow Cytometry Analyses

Figure 3:
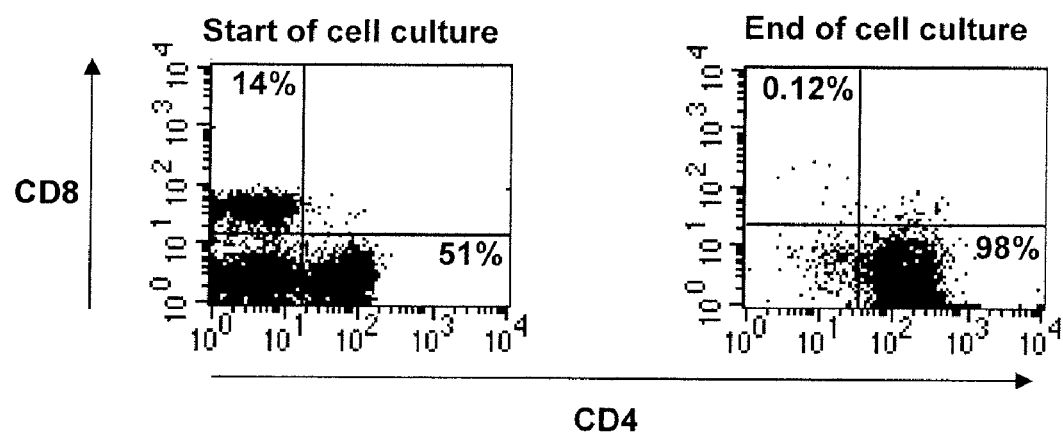
FIG. 3 illustrates that Phase I and Phase II activation results in expansion and enrichment of CD4$^+$ T helper cells.
Figure 4:
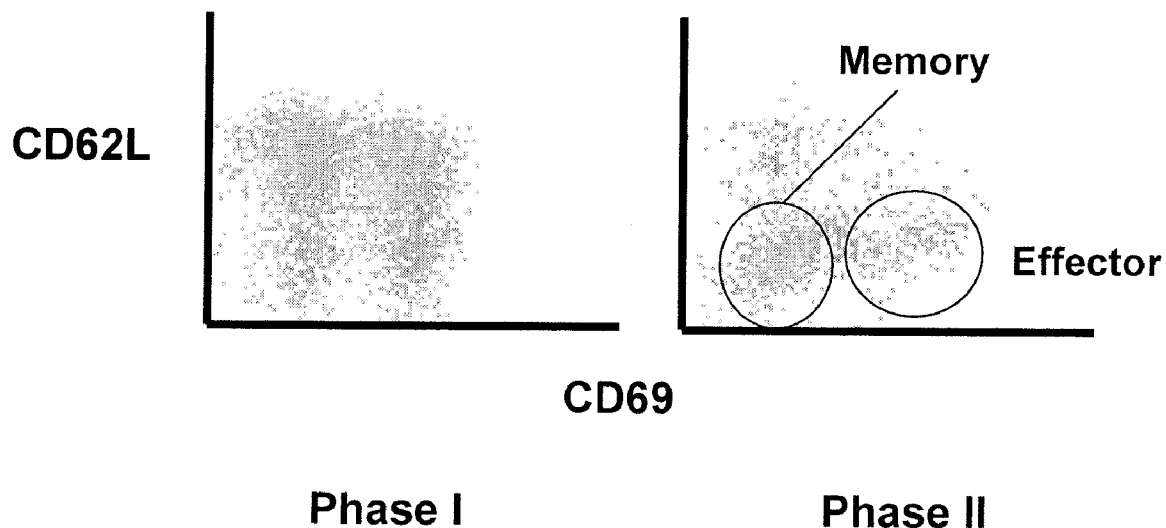
FIG. 4 illustrates that in Phase I the majority of cells are naïve CD62L+ cells or activated CD69+CD62L+ cells. After Phase II the majority of the cells are CD62L- and are composed of memory and effector CD4+ T helper cells. CD62L-T cells are not expressing the preferred lymph node homing molecule, thus they are seeking inflammatory areas in non-lymphatic organs.

Characterisation of cells was performed using flow cytometry initially on cells from the sentinel node, non-sentinel node, PBMC and from the tumour. From the sentinel node acquired lymphocytes in culture samples were taken every two to three weeks for flow cytometry analyses. Cells were incubated for 30 minutes in PBS supplemented with 2% FCS and 0.05% $NaN_3$ (FACS buffer) with antibodies against markers for immune cell subpopulations and for lymphocyte activation (FIGS. 3, 4 and 5). Antibodies conjugated with Fluorescein isothiocyanate (FITC) against the following markers were used: CD69, HLA-DR, CD45RA, CD25, conjugated with phycoerythrin (PE): CD62L, CD19, CD45RO, CD56, conjugated with Peridinin-Chlorophyll-Protein (PerCP): CD8, CD3, conjugated with allophycocyanin (APC): CD4, CD14, CD8.

Figure 7:
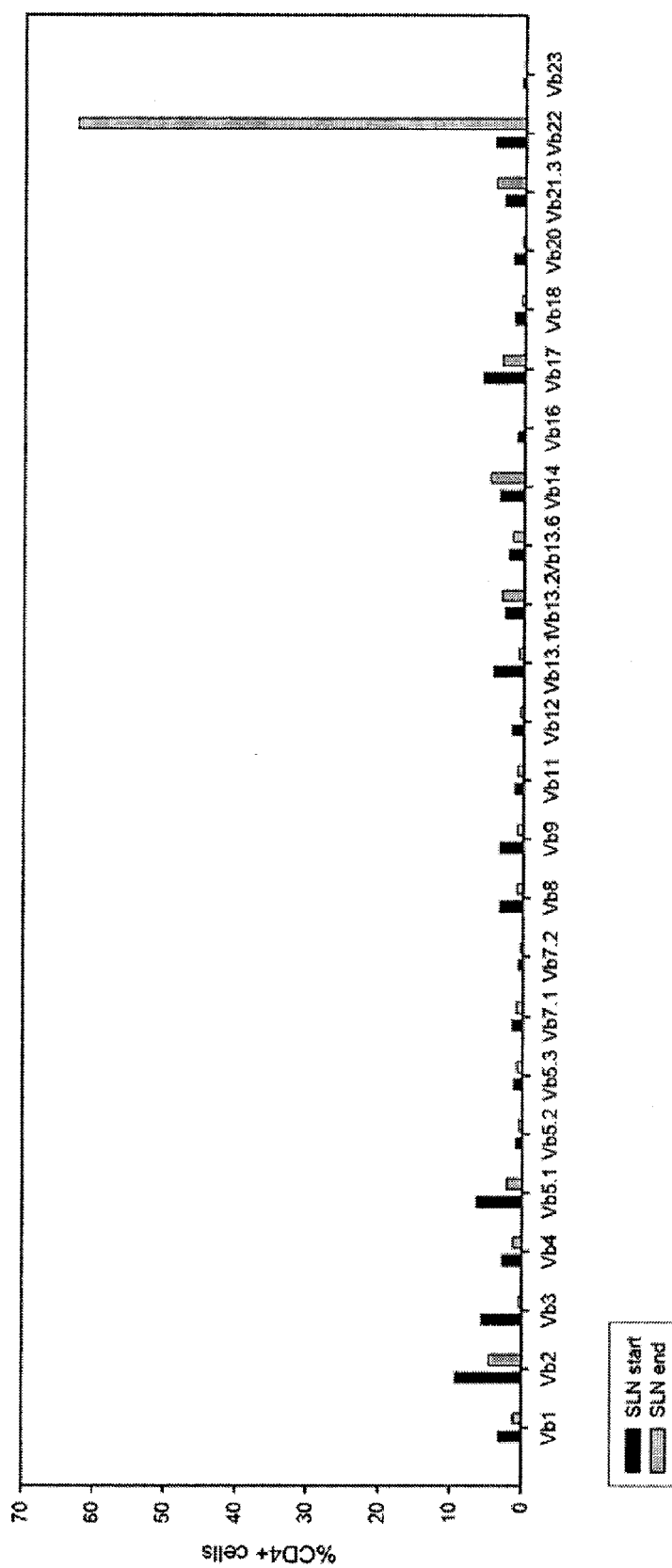
FIG. 7 illustrates that the expansion and activation protocol promotes the expansion of antigen specific T cell clones as investigated by the selective enrichment of TCR VP expression.

The Vβ-repertoire was examined using the Beta mark kit (Beckman Coulter), $5\times10^5$ cells/tube was stained in 10 µl of the 8 different vials containing mixtures of FITC, PE and dual-colour FITC-PE conjugated TCR VP antibodies and with the addition of CD8 PerCP and CD4 APC to each tube (FIG. 7).

Example 2

Treatment of Colon Cancer by Administering Tumour-Reactive T-Lymphocytes

Identification and Removal of Sentinel and Metinel Lymph Nodes from Colon Cancer Patients:

Sixteen patients diagnosed with colon cancer, six woman and ten men with an average age of 62 years were studied. Patients were histopathologically classified as Duke's C or D. There were also 5 patients with Duke's B with aggressive tumour characteristics such as ulcerations, vascular or perineural invasion. Patients 7 and 14 however had earlier been surgically treated due to colon cancer and now had recurrent disease with metastases to the liver. The local ethical committee approved the study and each patient gave informed consent.

Identification of sentinel or metinel nodes was done intraoperatively. Mobilisation of the colonic tumour site was achieved by division of peritoneal adhesions in order to facilitate inspection of tumour and mesentery. Injections of Patent blue dye (Guerbet, Paris) were distributed superficially in the serosa around the tumour. Within five minutes, one to three mesenteric lymph nodes were coloured blue, these sentinel nodes were marked with sutures and removed when the resection was complete. One non-sentinel mesenteric lymph node, distant from the tumour, was handled the same way.

The sentinel- and non-sentinel lymph nodes were cut in half and 1 mm thick slices were taken from the centre and the periphery. The rest of the lymph nodes were sent for histopathological examination according to routine procedure. A piece of the tumour, including a part of the invasive margin, was used for antigen preparation.

The lymphocytes obtained from the lymph nodes were then expanded as described in Example 1.

Administration of Tumour-Reactive T-Lymphocytes:

16 patients were treated with infusion of autologous lymphocytes expanded as described in Example 1. On average 74.7 million activated and clonally expanded T cells were administered as a transfusion. No toxic side effects like fever, chills, malaise, severe fluid retention, pulmonary oedema or respiratory distress were observed.

Follow-Up Evaluations

Figure 8:
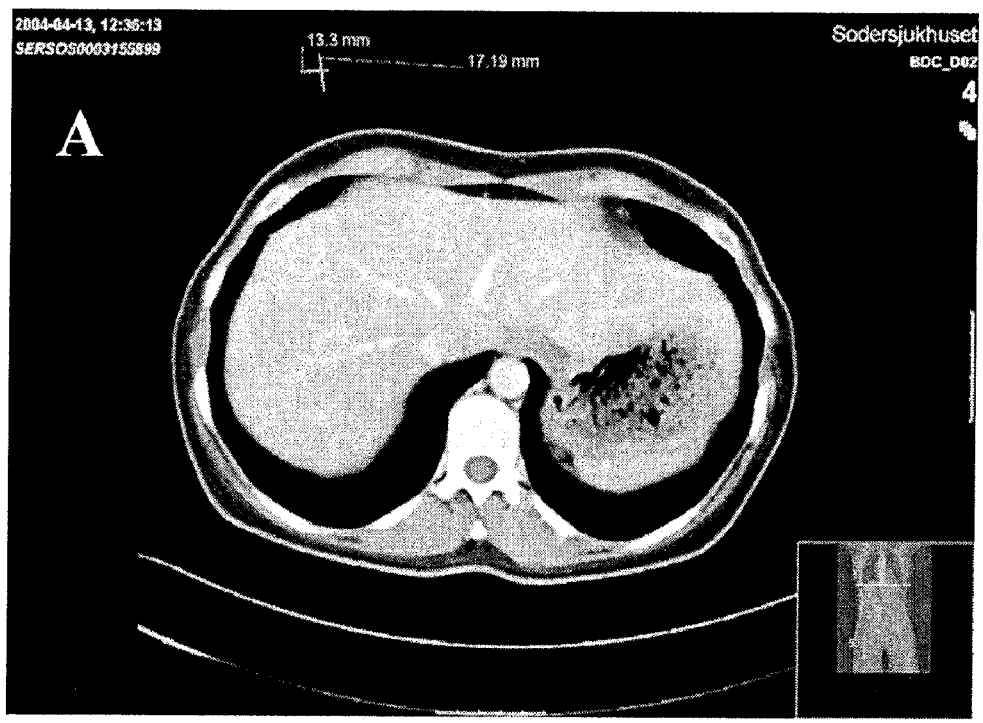
FIG. 8 A-D are CT scans of patient # 5. After transfusion of tumour-reactive lymphocytes the patient had total regress of liver metastases located in both lobes (which had been declared incurable by liver surgery), normalisation of CEA levels, disappearance of ascites and was physically well fit, exercising regularly.
Figure 8:
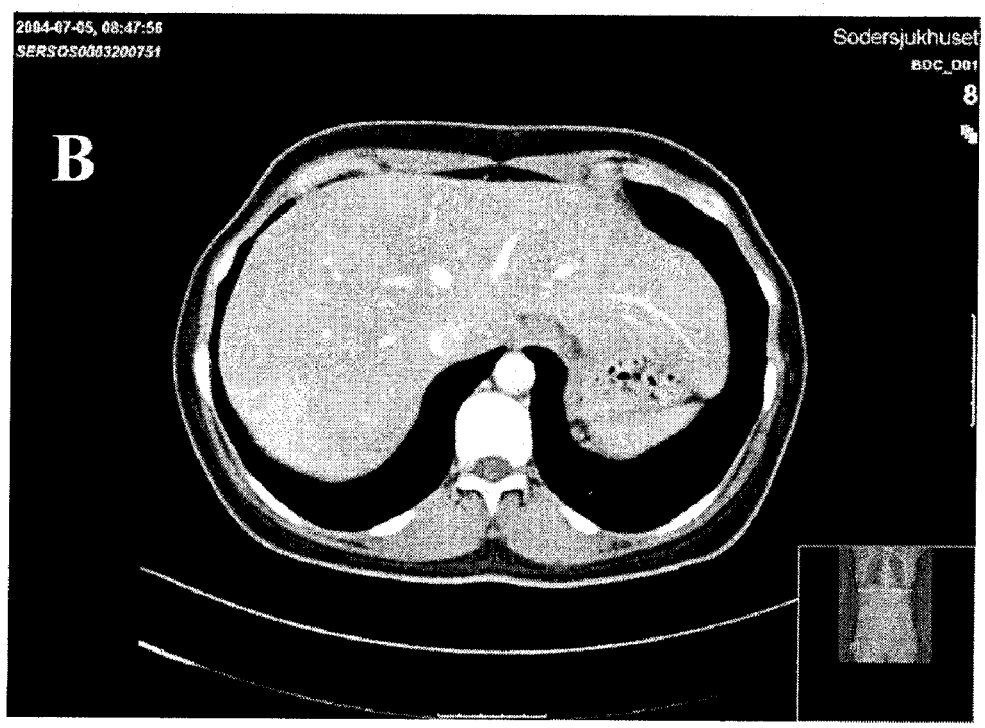
Figure 8:
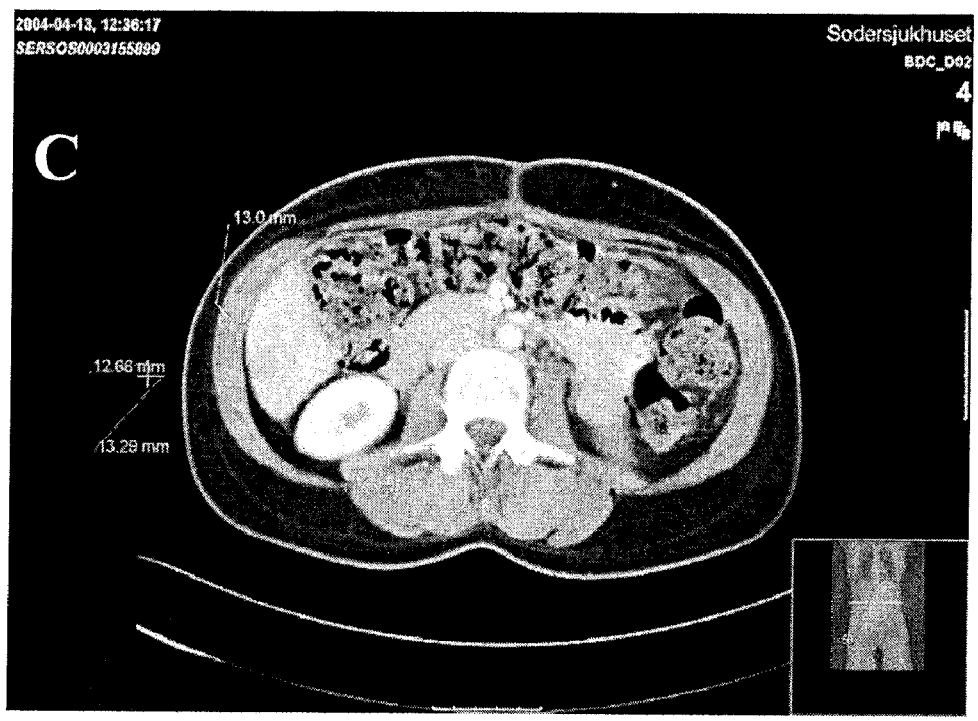
Figure 8:
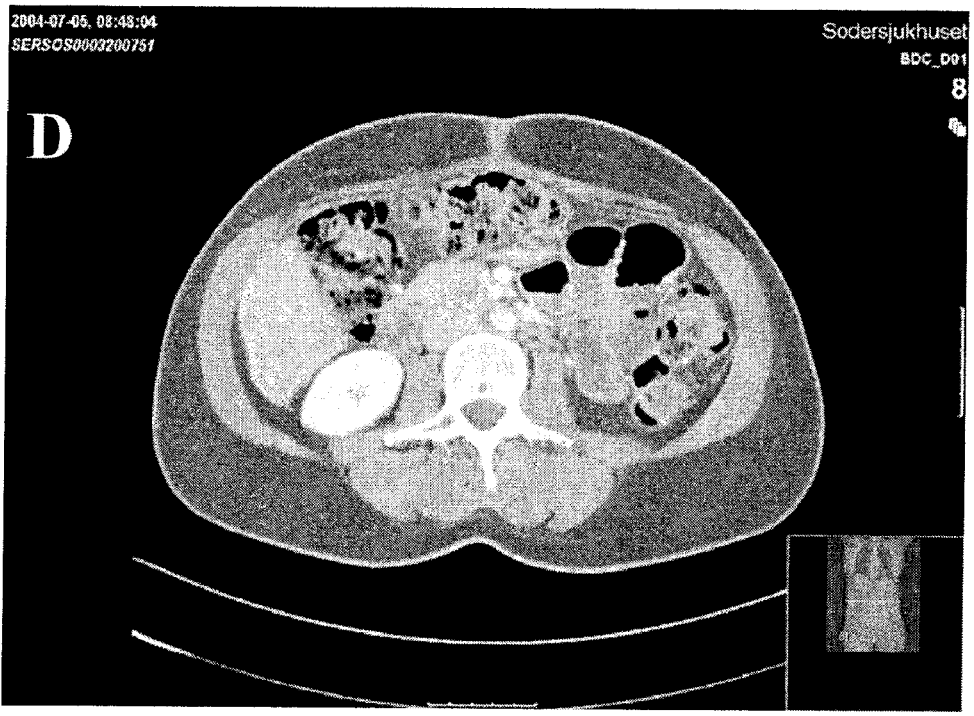
Figure 9:
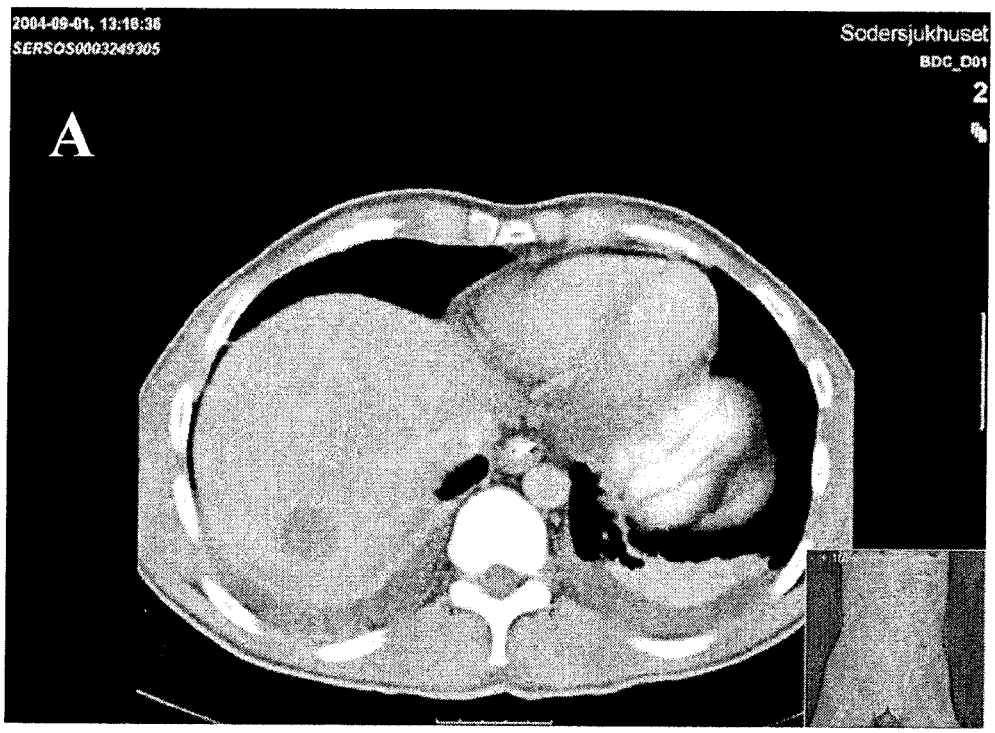
FIG. 9 A-F are CT scans of patient # 10. After transfusion the patient had regress of liver metastases and ascitic fluid. He was in fairly good health and further imaging showed stable disease.
Figure 9:
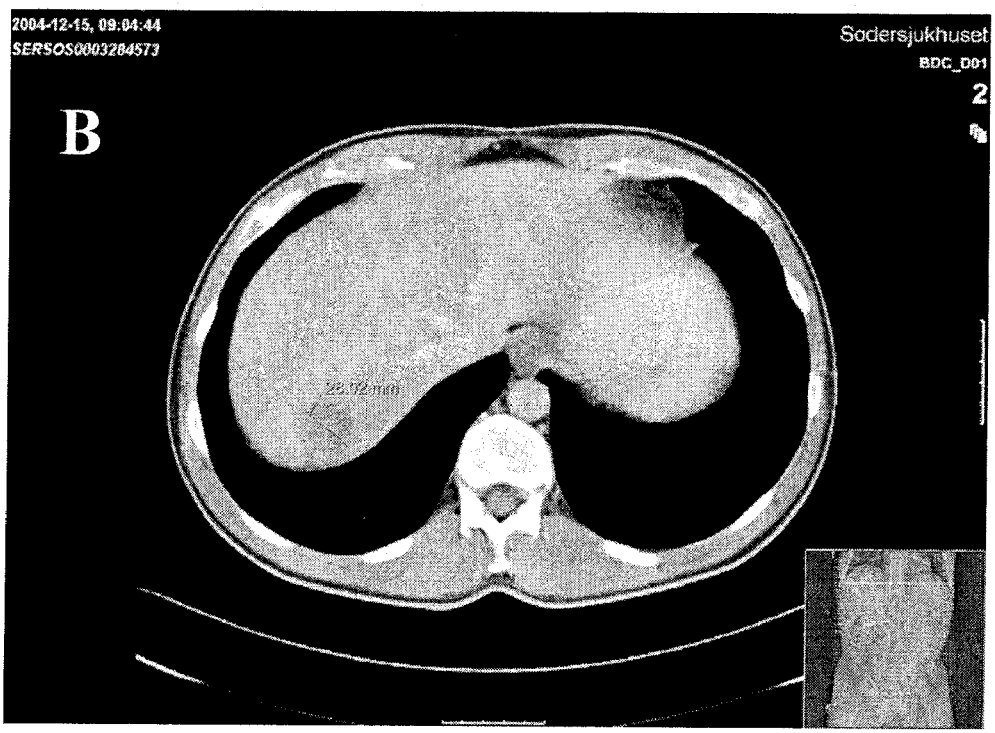
Figure 9:
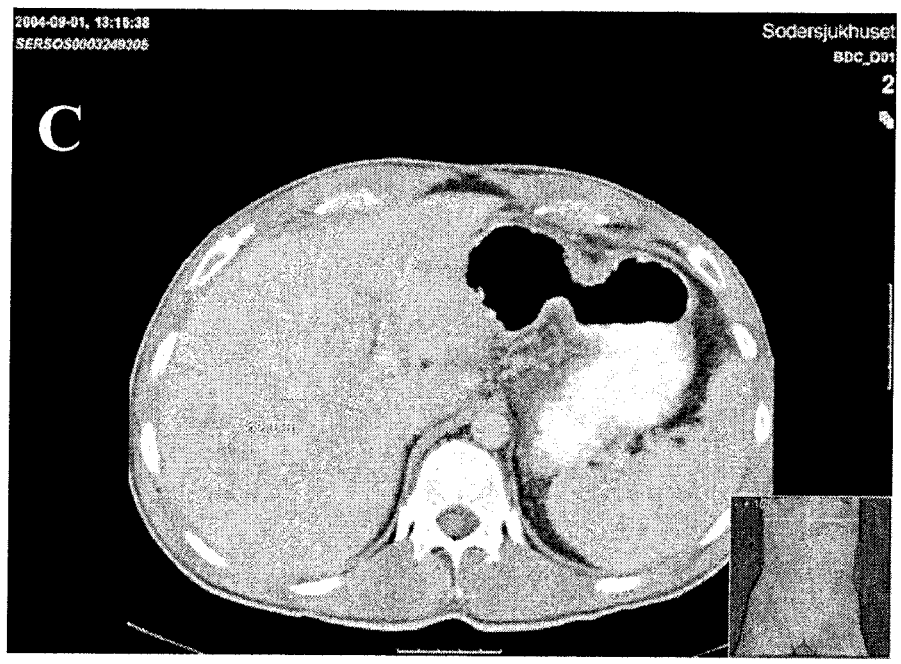
Figure 9:
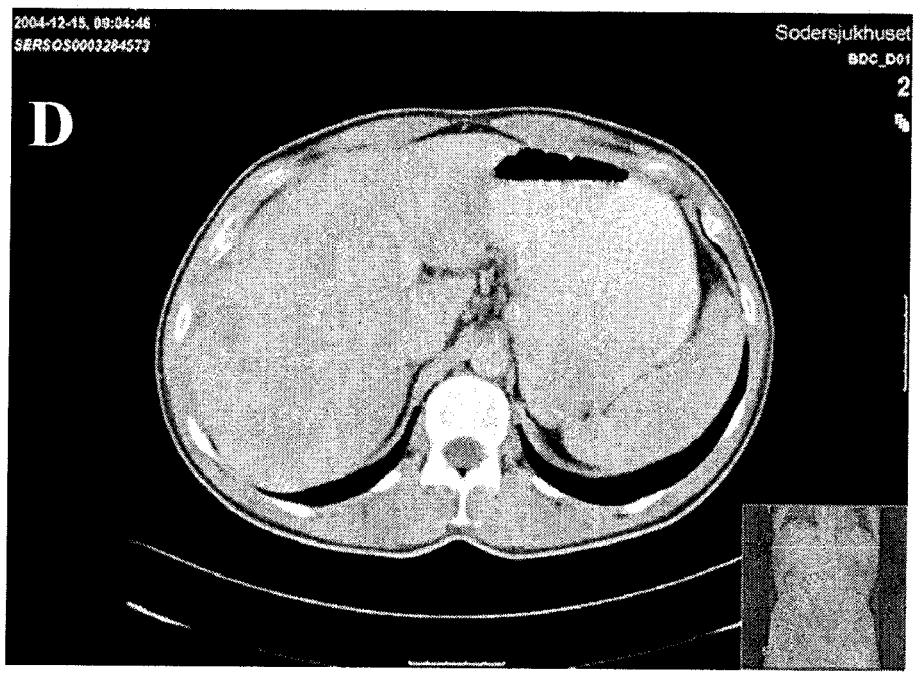
Figure 9:
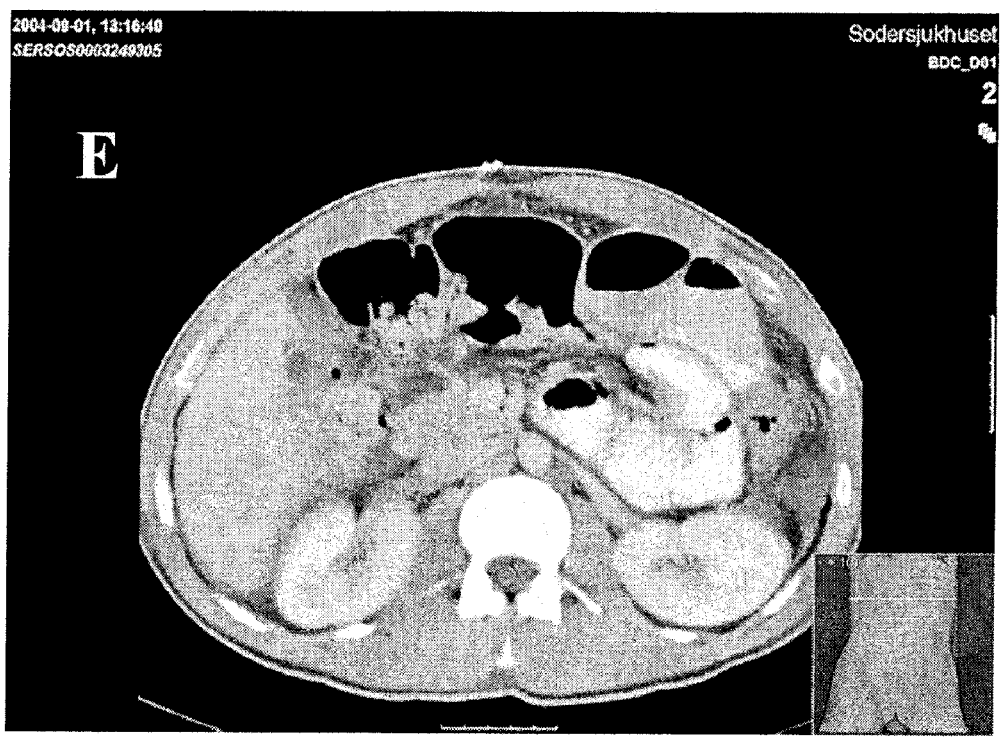
Figure 9:
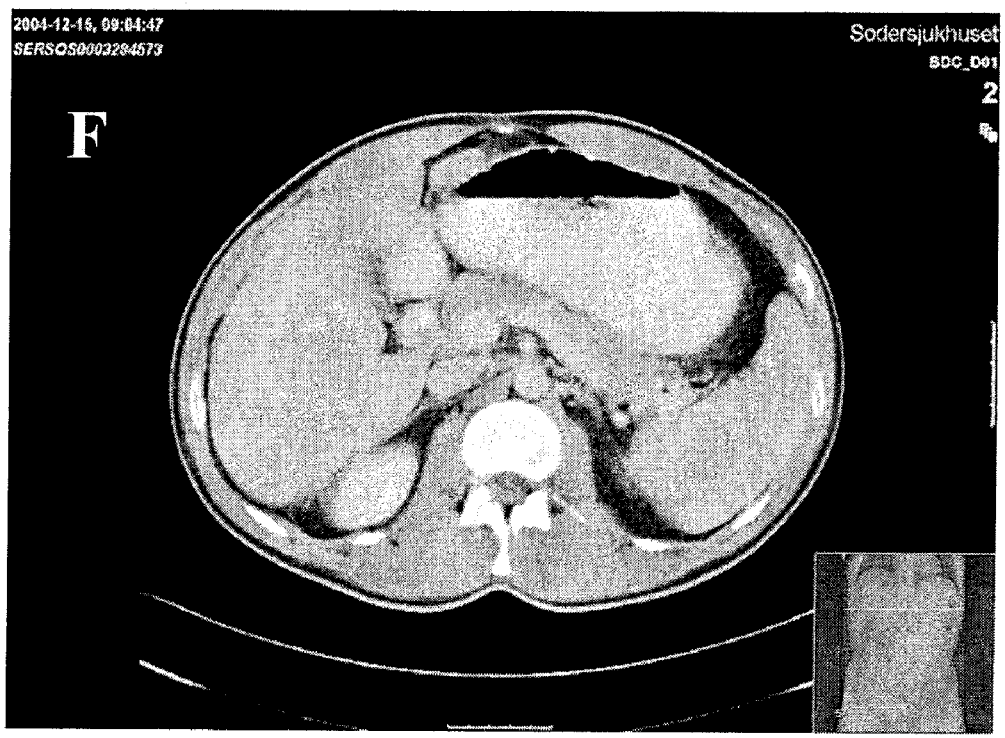
Figure 10:
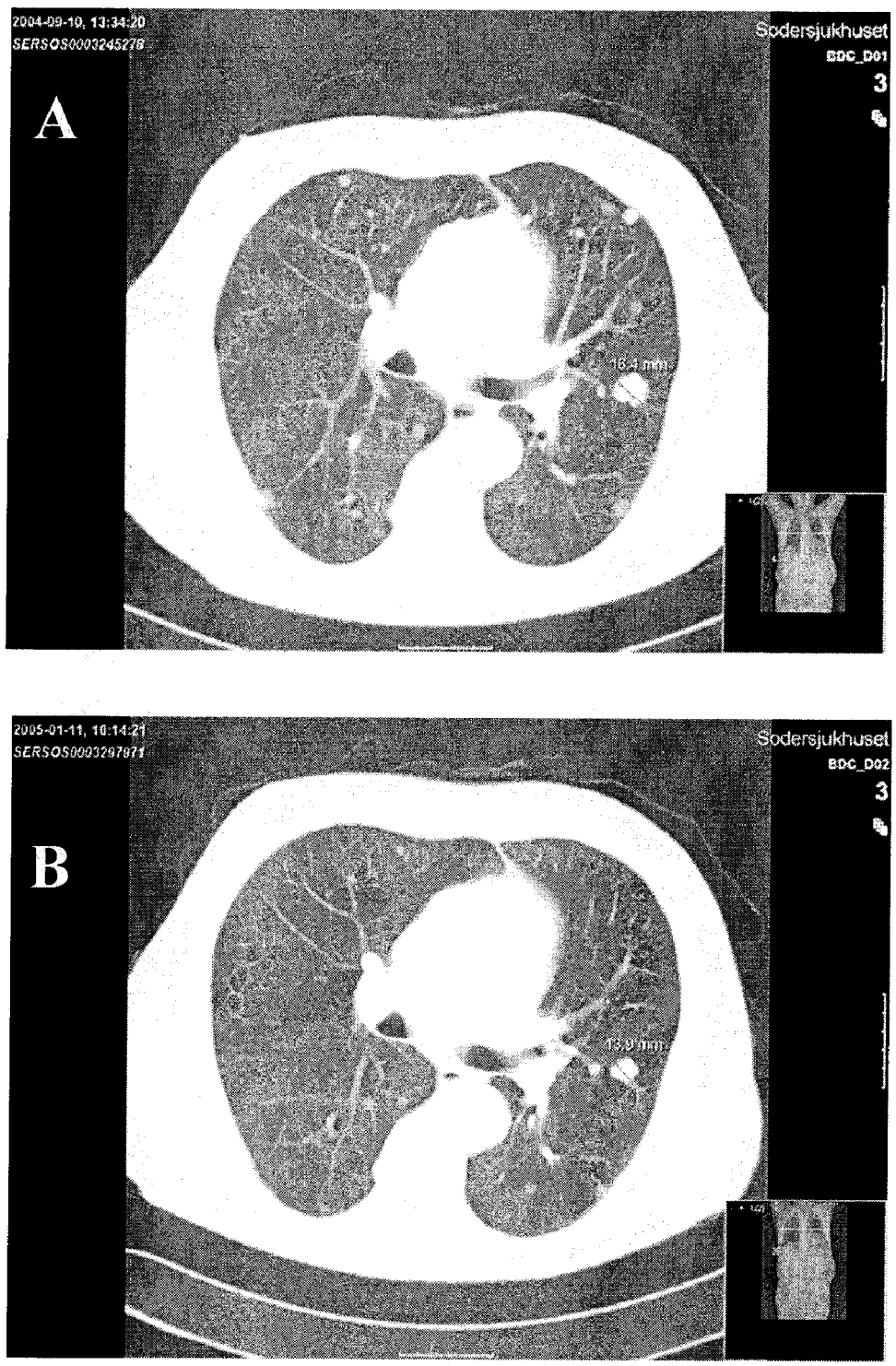
FIG. 10 A-H are CT scans of patient # 12. Three months after transfusion he had regress of metastases in the liver and lungs with almost a normalised CEA level at 5.9 (Normal<4.0), disappearance of ascites and he appears clinically healthy.
Figure 10:
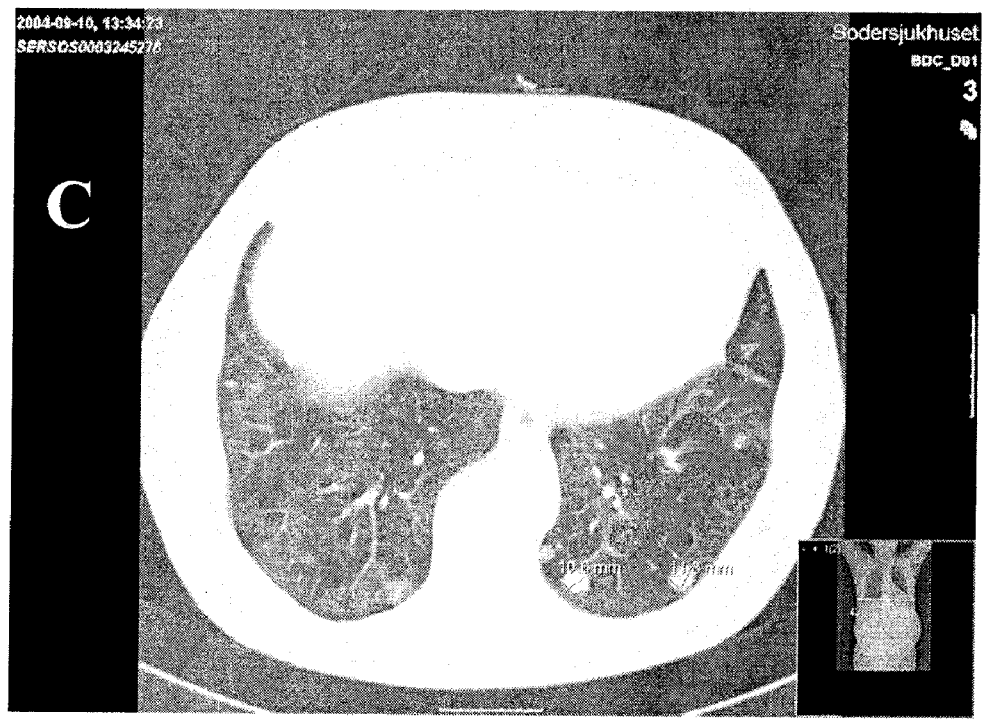
Figure 10:
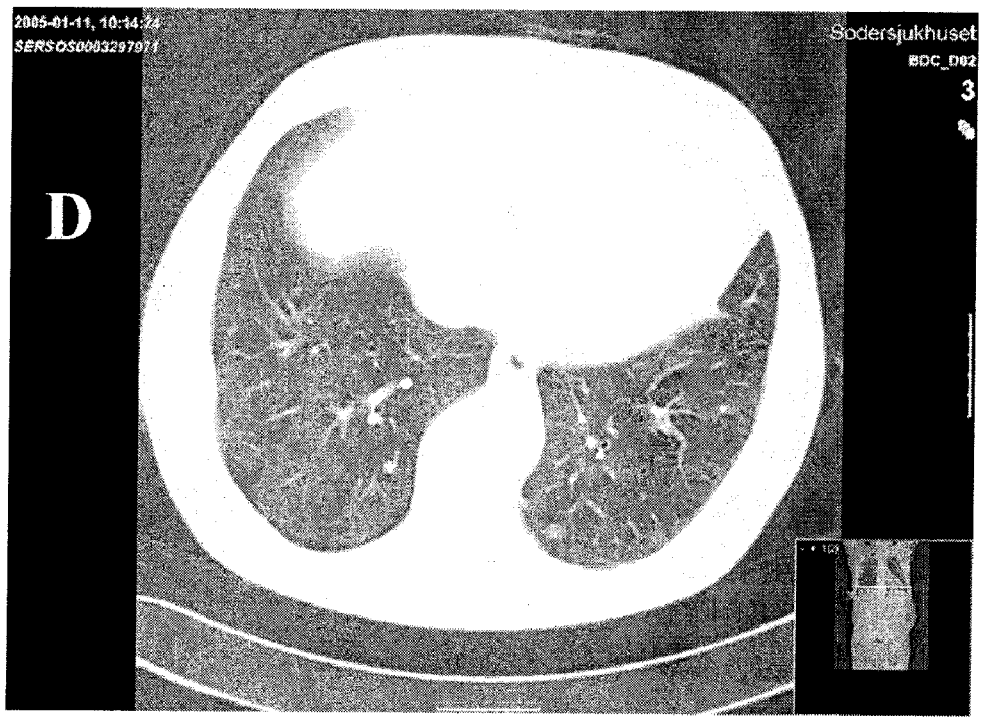
Figure 10:
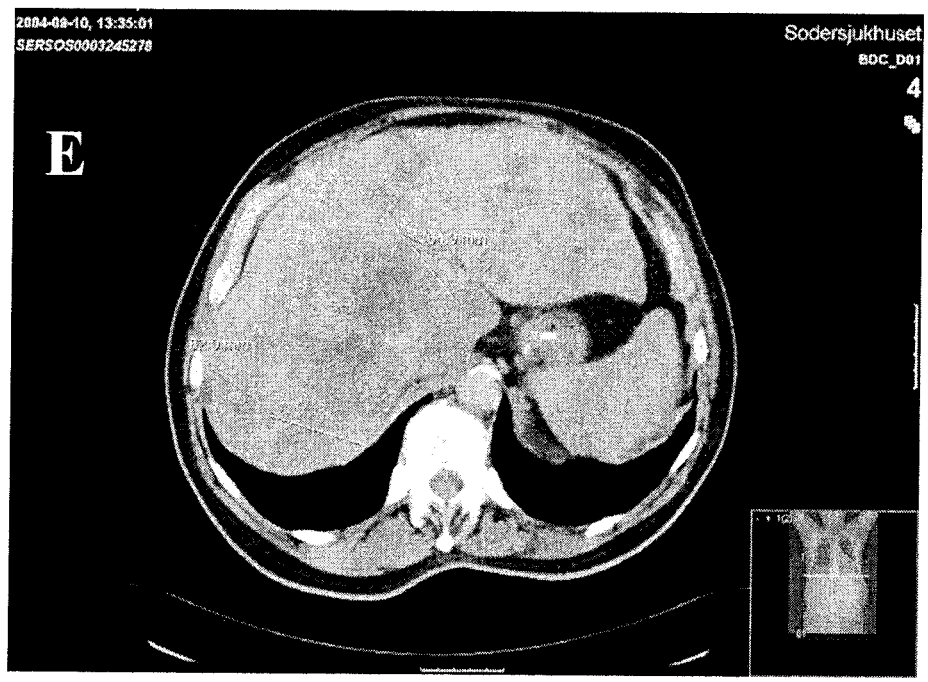
Figure 10:
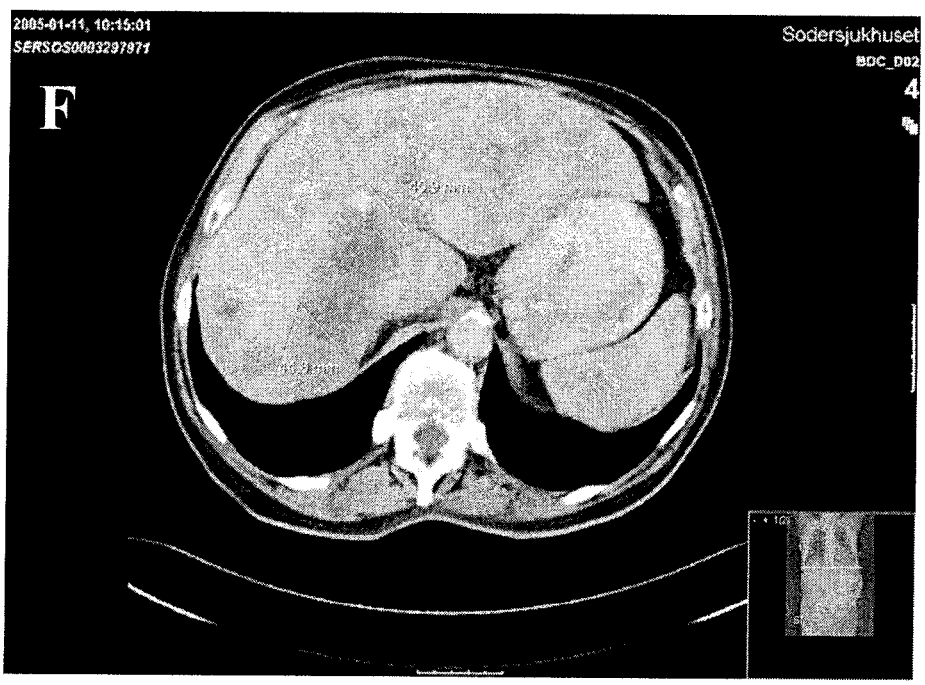
Figure 10:
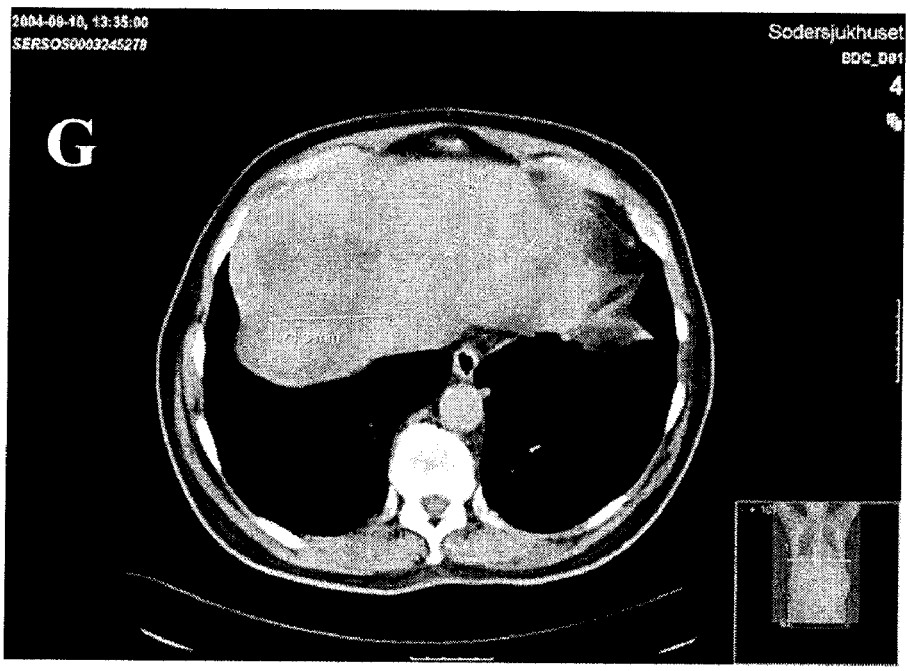
Figure 10:
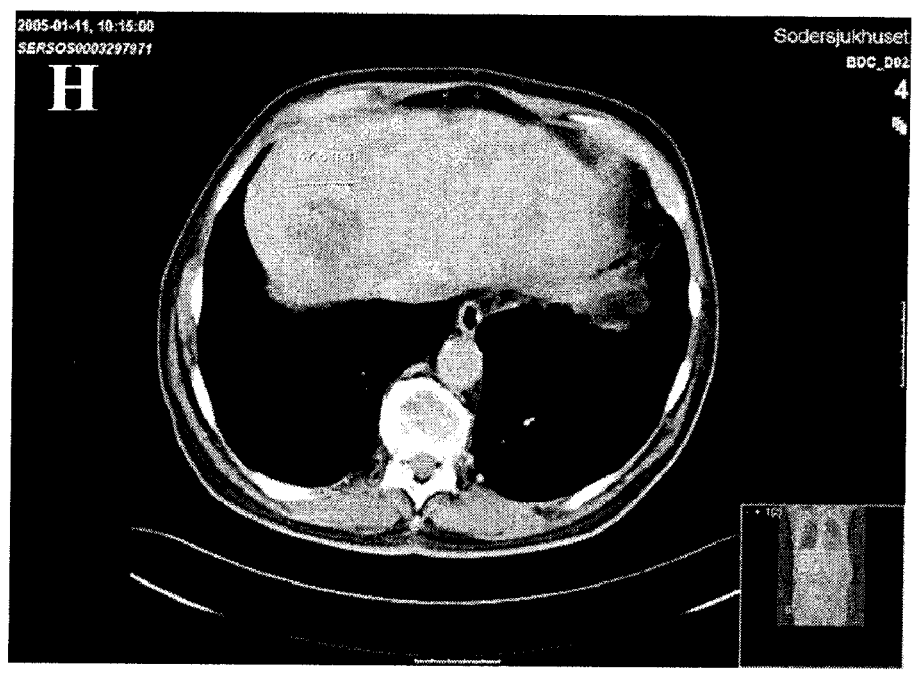
Figure 11:
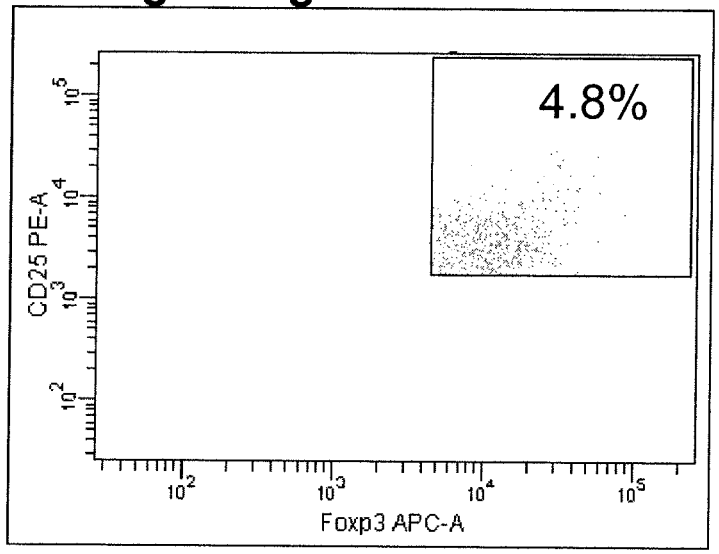
FIG. 11 shows T lymphocytes gated for the expression of CD4$^+$ which were stained for the expression of CD25 and the transcription factor FoxP3 at the beginning (A) and at the end (B) of an expansion. Initially (panel A), 4.8% of CD4+ T lymphocytes expressed FoxP3 and high levels of CD25, thus identified as Treg. At the end of the expansion a very small number of Tregs were present 0.3% (panel B).
Figure 11:
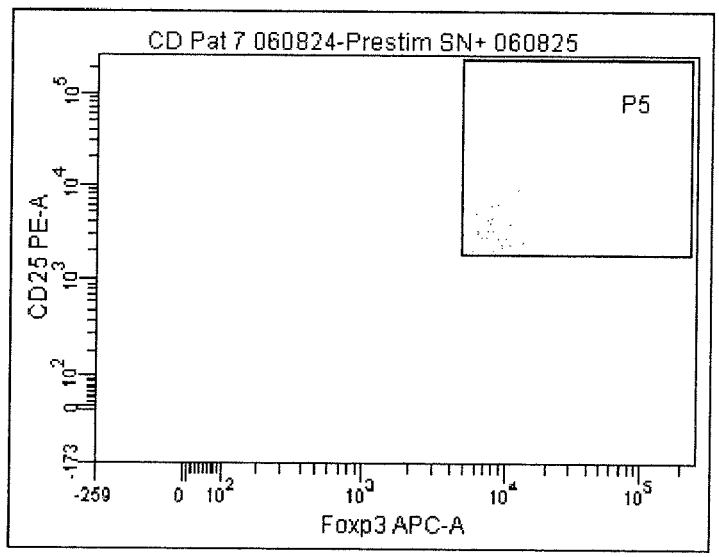

Follow-up included clinical examination every third to sixth month and control of CEA levels. All stage III and IV patients were in addition investigated with computer tomography of the thorax and abdomen. The patients were followed at regular visits on average for 13 months (range 5-20), median follow-up time was 13½ months. Out of the 16 patients who had been treated with infusion of autologous lymphocytes eight had known distant metastases at diagnosis. Four patients received their transfusions due to known recurrences and out of them three are still without signs of recurrences. One patient was operated due to a solitary liver metastases and has since then been without relaps. As it appears from FIG. 8 and FIG. 9, one patient with liver metastases located in both lobes (which had been declared incurable by liver surgery) had total regress of liver metastases after transfusion of tumour-reactive lymphocytes, and furthermore had normalisation of CEA levels, disappearance of ascites and is physically well fit, and exercising regularly. One further patient with liver metastases had regress of liver metastases and ascetic fluid after transfusion (see FIGS. 10, 11 and 12). One patient had three months after transfusion regress of metastases in the liver and lungs (see FIGS. 13, 14, 15, and 16) with almost a normalised CEA level at 5.9 (Normal<4.0), disappearance of ascites and he appears clinically healthy.

Results

Sixteen patients with colon cancer or solitary colorectal liver metastases were operated on at the South Stockholm General Hospital and included in the study. The primary locations of the tumours were three in caecum, 4 in colon ascendens, 1 in colon descendens, 7 in the sigmoid colon and 1 in rectum. Seven right-sided hemicolectomies, 1 left-sided hemicolectomy, 7 sigmoid resections and 1 rectumamputation were performed. Two patients had earlier been operated on with rectumamputation and sigmoid resection; they now underwent partial liver resections due to liver metastases. One patient had recurrences at two abdominal locations and had earlier been operated due to a tumour in the caecum. At our operation two sentinel nodes draining the metastasis were identified, one in the colonic mesentery and one in the mesentery of the small intestine. An extended resection of the anastomotic ileocolonic region with mesentery was done.

In all patients, one to three (average 2.1) sentinel node(s) were identified intraoperatively by peritumoural patent blue injections. Among the patients with primary colonic resection on average 15.8 lymph nodes were retrieved from each specimen. After histopathological investigation of these lymph nodes five patients were classified as Duke's C and 5 patients as Duke's B, all of them were classified as high-risk tumours due to growth of tumour cells along nerves and in vessels at pathological anatomical investigation. Five patients had distant metastases and were at time of metastatic resection classified as Duke's D. Two patients of them had solitary liver metastases. In addition sentinel nodes were also analysed by FACS (Fluorescence activated cell sorter) and antibodies against cytokeratin 20, which is expressed by colon cancer tumours, for the purpose to detect micrometastases. The cytokeratin 20 assessments of lymph nodes by flow cytometry were in agreement with the pathological anatomical diagnosis (not shown) except in one case where a false negative sentinel node (according to histopathological analysis) was positive in the cytokeratin 20 FACS analysis.

The sentinel node is the first lymph node draining the tumour and is therefore the first site of lymph node metastasis (Dahl et al), but the sentinel node is also the primary site for the activation of the immune system. Tumour cells, debris, necrotic cells and antigen presenting cells accumulate in the sentinel node where presentation, activation and clonal expansion of T cells directed against the tumour occur. The present inventors took advantage of this population of in vivo expanded T cell population of sentinel node acquired lymphocytes for in vitro cell culture, expansion and transfusion.

Sentinel node acquired lymphocytes is a population of T cells activated and clonally expanded against tumour antigens that can efficiently be harvested during the surgical procedure. In contrast to recent immunotherapy trials focusing on cytotoxic T cells, the aim of the present inventors was to create a protocol for in vitro enhancement of the in vivo initiated clonal expansion of T helper cells. T helper cells seem to be necessary for the effective function of cytotoxic T cells and for the creation of memory cells. Furthermore, in a T cell receptor transgenic system targeting an islet cell antigen, the transfusion of Th1 cells was found to be sufficient for the β cell destruction and development of diabetes mellitus. In vitro culture of sentinel node acquired lymphocytes resulted in a Th1 activation and clonal expansion of T helper cells as indicated by the dominant production of the hallmark Th1 cytokine IFN-γ and the enrichment of a restricted TCR Vβ repertoire. The tumour homogenate used to expand the T cells is likely to be endocytosed and processed by antigen presenting cells for class II presentation leading to activation of $CD4^+$ T helper cells resulting in expansion favouring T helper cells. By cross presentation antigens taken up by endocytosis may be processed and presented in the class I pocket resulting in activation of $CD8^+$ cytotoxic T cells. Interestingly, in some cases the inventors found clonal expansion of both $CD4^+$ and $CD8^+$ T cells.

The average number sentinel node acquired lymphocytes at start of expansion was 107.4 million cells (range 3.6-509 millions, median 70 millions). Cells were characterised by flow cytometry. The ratio between $CD4^+$ and $CD8^+$ cells at start was in average 4.9 (range 0.36-10, median 5.4) indicating an expansion $CD4^+$ T helper cells in sentinel nodes compared to the CD4/CD8 ratio in peripheral blood (normal range 1.0-2.5) (FIG. 2A). In addition B lymphocytes (CD 19) and natural killer (NK) cells (CD 56) were present in sentinel nodes (not shown). The cells were held in culture in average 36.1 days (range 23-58 days), median 33 days. Cells were monitored closely by flow cytometry at least weekly. Initially the total number of cells decreased. B cells and NK cells disappeared almost completely and the number of $CD8^+$ T killer cells was diminished. The culture procedure used promoted mainly the expansion of T helper cells since the average CD4/CD8 ratio was 92.5. Restimulation with autologous tumour antigen resulted in clonal expansion of tumour reactive T cells as assessed by investigating the T cell receptor Vβ repertoire of sentinel node acquired lymphocytes before and after in vitro culture.

Before transfusion expanded T cells were functionally tested against autologous tumour antigens by measuring activation and cytokine production of the Th1 cytokine IFN-γ and the Th2 cytokine IL-4. In vitro expanded sentinel node acquired lymphocytes responded upon restimulation with tumour antigen with the production of IFN-g and no or very little IL-4 indicating that the expanded T cells were functional and Th1 responsive.

Six patients with Duke's D were treated in the study. Two patients staged as Duke's D at surgery with metastases to the liver and to the lungs and liver, respectively displayed marked regression of disease (pat 5 and 12). After transfusion of lymphocytes the first patient had total regress of liver metastases located in both lobes (which had been declared incurable by liver surgery) (FIG. 3) normalisation of CEA levels, disappearance of ascites and appear healthy. Patient 12 shows regress of metastases in the liver and lungs with almost a normalised CEA level at 5.9 (Normal<4.0), disappearance of ascites and he appears clinically healthy. Patient 1 displayed a regression of the size of liver metastasis, and initially a decrease in CEA levels, disappearance of ascites and she was in excellent shape when she suddenly died (day 191), what appears to have been a lung embolus. Two Duke's D patients display stable disease without progression of metastasis or increase in CEA levels. The oldest patient no 7 in the study displayed stable disease for five months, but thereafter CEA levels started to increase and she died at age 83. No autopsy was performed. One patient was staged as Duke's C at surgery but soon developed metastases to the liver and lungs (Duke's D), but following transfusion and chemotherapy a regress of the lung and liver metastases were seen with only slightly elevated CEA levels. The patients classified as Duke's C all have normal CEA levels and appear without any signs of radiological or clinical recurrence of disease. Four of the Duke's B patients are healthy with normal CEA levels and have no signs of recurrent disease. Patient no 9 classified as Duke's B, but with an aggressive growing tumour shows signs of recurrent disease with elevated CEA levels (67) and signs of liver metastases.

To investigate the fate of transfused T cells the present inventors analysed T cell proliferation against tumour extract in peripheral blood. As mentioned before, they could not demonstrate any T cell reactivity in peripheral blood against autologous tumour antigens in any of the patients prior to transfusion. However, we were able to detect T cell proliferation against autologous tumour antigens in peripheral blood in all investigated patients up to 10 months after transfusion indicating the presence of clonally expanded circulating tumour-reactive T cells.

Summary of Patient Characteristics

Below is a table of all participants in the study, sorted after Duke's classification at surgery:

| Age/Sex | Duke's Classification | Infused cells (×10⁶) | CD4/CD8 [a] | IFN-γ (pg/ml) | Overall survival (months) | Response |
|---|---|---|---|---|---|---|
| 67/M | B | 4 | 92/0.2 | ND | 31 | SD |
| 67/F | B | 8 | 15/51 | ND | 30 | SD |
| 71/M | B | 50 | 74/15 | 2091 | 29 | SD |
| 74/M | B | 63 | 64/22 | ND | 29 | SD |
| 66/M | B | 152 | 82/1.5 | 1411 | 27 | SD |
| 64/F | C | 110 | 64/25 | ND | 34 | SD |
| 58/F | C | 16 | 77/18 | 417 | 23 | SD |
| 61/F | D | 1 | 3.7/35 | ND | 6 | SD |
| 47/M | D | 80 | 24/16 | ND | 36 | CR |
| 54/M | D | 40 | 37/24 | ND | 36 | SD |
| 65/M | D | 270 | 82/15 | ND | 36 | CR |
| 42/F | D | 80 | 66/11 | ND | 33 | CR |
| 82/F | D | 40 | 98/0.1 | ND | 6 | SD |
| 74/M | D | 130 | 73/22 | 142 | 30 | CR |
| 33/M | D | 72 | 72/1.5 | 908 | 12 | PR |
| 66/M | D | 25 | 37/27 | 764 | 26 | PR |

[a] The numbers represent the percentage of CD4 and CD8 positive cells detected with FACS.

Discussion

To the knowledge of the present inventors, sentinel or metinel node-based immunotherapy in patients with colon cancer has never been presented before. Thus, this is the first attempt to use lymphocytes acquired from sentinel or metinel nodes for therapy. There are some major differences between the present study and e.g. treatment with high-dose IL-2 (Rosenberg). Firstly the use of sentinel node acquired lymphocytes that have been in vitro stimulated by autologous tumour homogenate and APCs, causes a highly specific cellular immune response towards the tumour. Only T cells with high affinity to the primary tumour will survive until transfusion. In a systemic generalized treatment with high-dose IL-2 intravenously to patients all lymphocytes will be equally stimulated and reasonably only a very small fraction of them are tumour specific. The present inventors believe that since the sentinel node(s) are the first draining lymph nodes to a tumour there will be an excessive accumulation of tumour specific lymphocytes. The proliferation and transfusion of true tumour recognising T cells should create a massive tumour specific reaction. Secondly the high-dose IL-2 regimen causes high-toxicity and severe complications, long treatment periods and high costs. The transfusions according to the present method have been given without complications during about one hour and the patients are often discharged the same day. Thirdly, the present protocol aim towards expansion of T helper cells from sentinel nodes, in contrast to expansion of cytotoxic T cells harvested as tumour infiltrating lymphocytes.

This study shows that freshly isolated sentinel node acquired lymphocytes possesses a proliferative ability in vitro against autologous tumour homogenate and can without complications be transfused to the patient as adoptive immunotherapy. There is a strong indication to that treatment with expanded sentinel node acquired lymphocytes may improve the outcome of patients with high-risk or disseminated colon cancer, as well as patients suffering from types of solid cancer.

Example 3

Expansion of Lymph Node Acquired Lymphocytes from Patient with Gallbladder Cancer On day one, cell cultures containing approximately 35 million (Culture 1) and 5 million cells (Culture 2) was set up.

Throughout the whole culturing period, cells were kept in incubator at 37° C. and 5% $CO_2$ and 240 IU IL-2/mL media added every 3-4 days.

Initially, both cultures contained a high proportion of red blood cells which eventually decreased as only lymphocytes proliferated in the cultures.

On day 3, autologous tumor extract were added to both cultures at a concentration of 1/100.

On day 10, phase II was initiated in both cultures by adding radiated antigen presenting cells, autologous tumor extract and interleukin-2 (240 IU/ml) to the cultures. At this stage, the cultures contained approximately 45 million and 15 million lymphocytes, respectively.

Cultures were maintained regularly by keeping the cell concentration at approximately 3 million cells/ml.

Cells from both cultures were harvested on day 25 and a cell transfusion solution containing cells from both cultures was prepared.

The final number of cells were 94 million for Culture 1 and 79 million for Culture 2. Culture 1 contained approximately 85% CD4 T cells and 5% CD8 T cells.

V beta profiling of Culture 1 revealed high proportions of V beta profiles 1, 2 and 22, indicating that clonal expansions of cells with these profiles had occurred.

Example 4

Expansion of Sentinel Node Acquired Lymphocytes from Patient with Small Intestine Cancer On day one, lymphocytes were extracted from three sentinel lymph nodes and put into separate cultures (Culture 1-3).

Main conditions of the cell cultures were as described in example 3.

The cultures initially contained 27, 37, and 6 million cells, respectively.

Analysis of cultures on day 2 revealed CD4/CD8 ratios in the cultures of 79% CD4/8% CD8 for Culture 1, for Culture 2 46%/8%, and for Culture 3 27%/4%.

Early analysis revealed the Cultures 2 and 3 both had strong tumour presence. However, at the end of culture both cultures were free of tumour cells, indicating that only T cells had proliferated in these cultures.

On day 3, autologous tumor extract were added to all cultures at a concentration of 1/100.

On day 15, phase II were initiated in all cultures by adding radiated antigen presenting cells, autologous tumor extract and interleukin-2 (240 IU/ml) to the cultures. At this stage, Culture 1 and 2 contained approximately 50 million cells and Culture 3 about 30 million cells.

At beginning of phase II, the CD4/CD8 ratios were 74%/10% in Culture 1, 66%/11% in Culture 2 and 77%/7% in Culture 3.

On day 25, the cells from all cultures were harvested and a cell transfusion solution containing cells from all cultures was prepared. The total final number of cells in all cultures was 136 million.

Analysis of CD4/CD8 ratios was done the day before harvest, with the following results:

Culture 1: 59%/21%, Culture 2: 58%/24%, and Culture 3: 57%/14%. The results of the analysis indicated that both CD4 and CD8 T cells had proliferated in Phase II.

Example 5

Expansion of Sentinel Node Acquired Lymphocytes from Patient with Mesothelioma

Lymphocytes were acquired from four different Sentinel Nodes draining a mesothelioma tumor originating in pleura of a patient. On day one, one culture from each sentinel node was set up.

Throughout the whole culturing period, cells were kept in incubator at 37° C. and 5% $CO_2$ and 240 IU IL-2/mL media added every 3-4 days.

Initial data for cell number and CD4/CD8 ratios were as follows:

| Culture 1: | 39 million | 18% CD4/4% CD8 |
| Culture 2: | 97 million | 25%/5% |
| Culture 3: | 32 million | 26%/8% |
| Culture 4: | 17 million | 28%/9% |

Initial analysis of showed presence of tumor cells in all cultures (10-15%). Especially Cultures 3 and 4 showed strong presence of tumor cells. However, during the course of culturing all cultures presented decreased tumor cell presence. At day 21 tumor presence had decreased to 0.5-1.5% in all four cultures, indicating that only T cells had proliferated in the cultures.

On day 3, autologous tumor extract were added to all cultures at a concentration of 1/100.

On day 14, phase II were initiated in all cultures by adding radiated antigen presenting cells, autologous tumor extract and interleukin-2 (240 IU/ml) to the cultures.

Cell count and analysis of T cell characteristics was done on day 21 for all cultures, revealing the following data:

| Culture 1: | 200 million | 63% CD4/21% CD8 |
| Culture 2: | 350 million | 77% CD4/13% CD8 |
| Culture 3: | 350 million | 57% CD4/28% CD8 |
| Culture 4: | 350 million | 49% CD4/34% CD8 |

Results indicate expansion of both CD4 and CD8 cells in all cultures.

Figure 12:
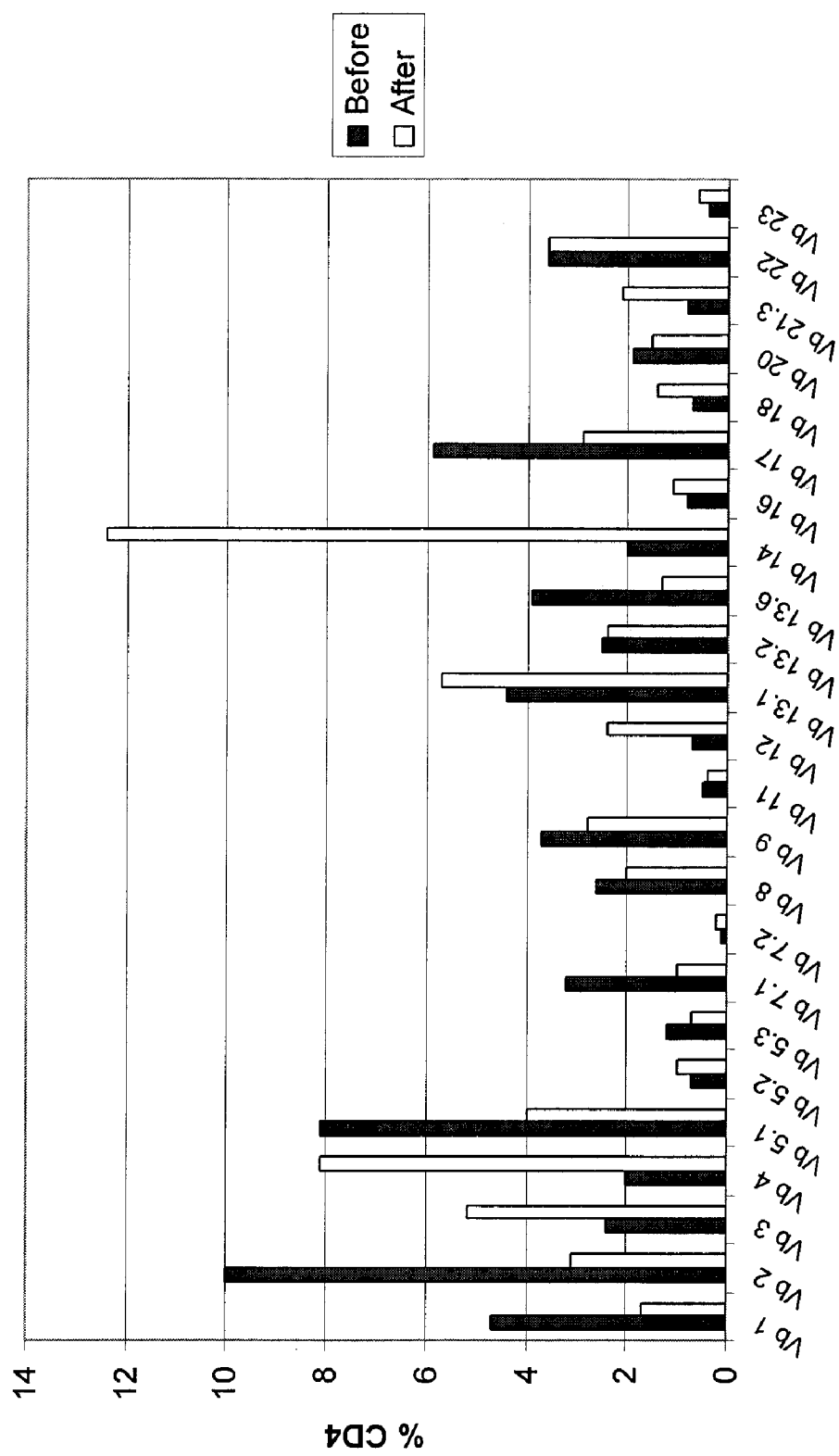
FIGS. 12 and 13 show results of analysis of Vbeta profiles of CD4 T cells from patient with mesothelioma (described in example 5). Analysis was performed on day 2 (Before) and day 24 (After) of the expansions. Clonal expansion of CD4 T cells belonging to Vbeta groups 4 and 14 can be seen in Culture 1. A similar general pattern of clonal expansion can be seen in both cultures.
Figure 13:
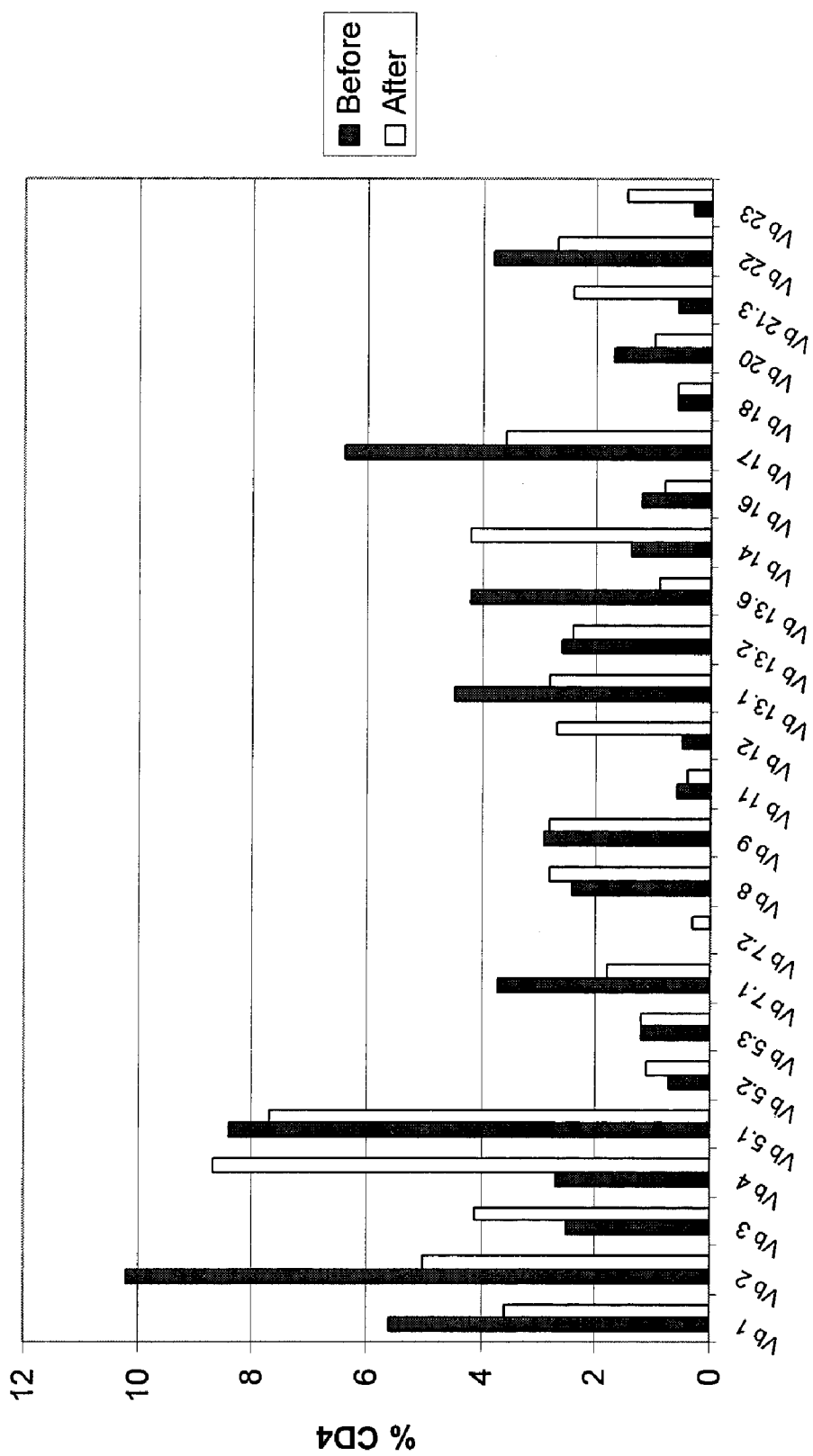

Analysis of the Vbeta profiles of Cultures 1 and 2 was performed on day 2 and on day 24 of the cell culturing period (see FIGS. 12 and 13). Results of the analysis clearly indicate that a clonal expansion of T cells belonging to Vbeta groups 4 and 14 had taken place. In culture 1, Vbeta group 4 had been expanded by a factor 4 and Vbeta group 14 had been expanded by a factor 6. Interestingly, a similar general pattern of clonal expansion pattern was seen in both cultures.

Specific Embodiments

The following is a list of specific embodiments of the present invention. It is to be understood that such embodiments are presented as exemplary only and that the present invention is to in no way be limited thereby.

1. A method for treating a patient suffering from a neoplastic disease selected from gall bladder cancer, hepato cellular cancer, ovarian cancer, small intestine cancer, lung cancer, mesothelioma, breast cancer, kidney cancer, pancreas cancer, prostate cancer, carcinoid cancer, leiomyosarcoma, or metastasis thereof, the method comprising
   i) identifying in a patient one or more sentinel and/or metinel lymph nodes draining a neoplasm selected from gall bladder cancer, hepato cellular cancer, ovarian cancer, small intestine cancer, lung cancer, mesothelioma, breast cancer, kidney cancer, pancreas cancer, prostate cancer, carcinoid cancer, leiomyosarcoma, or metastasis thereof,
   ii) resecting the one or more nodes and, optionally all or part of the tumour or metastasis,
   iii) isolating tumour-reactive T-lymphocytes from said lymph nodes,
   iv) in vitro expanding said tumour-reactive T-lymphocytes,
   v) administering the thus obtained tumour-reactive T-lymphocytes to the patient,
   wherein the T-lymphocytes are CD4+ helper and/or CD8+ T-lymphocytes.
2. A method according to embodiment 1 or 2, wherein the one or more lymph nodes are identified in step i) by injecting one or more lymph node locators into the patient.
3. A method according to any of the preceding embodiments, wherein the one or more lymph node locators are affinity based.
4. A method according to any of the preceding embodiments, wherein the one or more lymph node locators are non-affinity based.
5. A method according to any of the preceding embodiments wherein one or more lymph node locators are injected into, above, around, adjacent and/or under the tumour or metastasis.
6. A method according to any of the preceding embodiments, wherein the one or more lymph node locators are injected by a single injection.
7. A method according to any of embodiments 1-5, wherein the one or more lymph node locators are injected by multiple injections.
8. A method according to any of the preceding embodiments, wherein the one or more lymph node locators are injected by a non-surgical procedure.
9. A method according to any of embodiments 1-79, wherein the one or more lymph node locators are injected as part of a surgical procedure.
10. A method according to any of the preceding embodiments, wherein all or part of the tumour or metastasis is removed from the patient.
11. A method according to any of the preceding embodiments wherein the in vitro expansion step iv) comprises
   i) a first phase of stimulating tumour-reactive CD4+ helper and/or CD8+ T-lymphocytes with tumour-derived antigen together with at least one substance having agonistic activity towards the IL-2 receptor to promote survival of tumour-reactive CD4+ helper and/or CD8+ T-lymphocytes, and
   ii) a second phase of activating and promoting growth of tumour-reactive CD4+ helper and/or CD8+ T-lymphocytes, wherein the second phase ii) is initiated when the CD25 cell surface marker (or IL-2R marker) is down-regulated on T-lymphocytes.
12. A method according to embodiment 11, wherein the down-regulation is defined as that 5% or less of the T-lymphocyte population expresses CD25.
13. A method according to embodiment 11 or 12, wherein the T-lymphocytes are present in a culture medium.

14. A method according to embodiment 13, wherein the culture medium is a serum-free medium, such as, e.g. AIMV medium.

15. A method according to any of the preceding embodiments, wherein the first phase i) is initiated by adding the at least one substance having agonistic activity towards the IL-2 receptor.

16. A method according to embodiment 15, wherein the substance having agonistic activity towards the IL-2 receptor is IL-2.

17. A method according to embodiment 16, wherein IL-2 is added in a low dose, such as, e.g., from about 100 IU/ml culture medium to about 700 IU/ml culture medium, from about 100 IU/ml culture medium to about 600 IU/ml culture medium, from about 100 IU/ml culture medium to about 500 IU/ml culture medium, from about 100 IU/ml culture medium to about 400 IU/ml culture medium, from about 100 IU/ml culture medium to about 300 IU/ml culture medium and from about 100 IU/ml culture medium to about 200 IU/ml culture medium.

18. A method according to any of the preceding embodiments, wherein a further amount of the at least one substance having agonistic activity towards the IL-2 receptor is added regularly throughout phase i), such as, e.g., every $2^{nd}$, $3^{rd}$ or $4^{th}$ day of phase i).

19. A method according to embodiment 18, wherein the substance having agonistic activity towards the IL-2 receptor is IL-2.

20. A method according to embodiment 19, wherein the concentration of IL-2 added is from about 100 IU/ml culture medium to about 700 IU/ml culture medium, from about 100 IU/ml culture medium to about 600 IU/ml culture medium, from about 100 IU/ml culture medium to about 500 IU/ml culture medium, from about 100 IU/ml culture medium to about 400 IU/ml culture medium, from about 100 IU/ml culture medium to about 300 IU/ml culture medium and from about 100 IU/ml culture medium to about 200 IU/ml culture medium.

21. A method according to any of the preceding embodiments, wherein the tumour-derived antigen is added from day 2 to and including day 5 of the first phase i), such as, e.g., on day 2, on day 3, on day 4 or on day 5.

22. A method according to any of embodiments 11-20, wherein the tumour-derived antigen is added essentially at the same time as when phase i) is initiated or at the most up to 3 days thereafter.

23. A method according to any of the preceding embodiments, wherein the tumour-derived antigen is a denatured homogenate of a tumour.

24. A method according to any of the preceding embodiments, wherein the tumour-derived antigen is a protein, polypeptide or peptide.

25. A method according to any of the preceding embodiments, wherein the second phase ii) is initiated from day 17 to and including day 23 of the first phase i), such as, e.g. on day 17, on day 18, on day 19, on day 20, on day 21, on day 22 or on day 23.

26. A method according to any of the preceding embodiments, wherein the second phase is initiated by the addition of tumour-derived antigen to the T-lymphocytes for activating tumour-reactive CD25-negative T-lymphocytes.

27. A method according to embodiment 26, wherein the tumour-derived antigen is a denatured homogenate of a tumour.

28. A method according to embodiment 26, wherein the tumour-derived antigen is a tumour protein, polypeptide or peptide.

29. A method according to any of embodiments 26-28, which further comprises addition to the T-lymphocytes of antigen presenting cells together with the tumour-derived antigen.

30. A method according to embodiment 20, wherein the antigen presenting cells are irradiated peripheral blood leucocytes containing antigen-presenting B-cells and/or monocytes.

31. A method according to any of the preceding embodiments, wherein the second phase ii) comprises adding at least one substance capable of up-regulating IL-12R on the T-lymphocytes.

32. A method according to embodiment 31, wherein the substance(s) capable of up-regulating IL-12R on the T-lymphocytes is substance(s) having agonistic activity towards an interferon receptor.

33. A method according to embodiment 32, wherein the substance(s) having agonistic activity towards an interferon receptor is an interferon.

34. A method according to embodiment 33, wherein the substance(s) having agonistic activity towards an interferon receptor is interferon-$\alpha$.

35. A method according to any of embodiments 31-34, wherein the substance(s) capable of up-regulating IL-12R on the T-lymphocytes, such as, e.g. a substance having agonistic activity towards an interferon receptor, is added when the level of IL-12 is at least 1 fold, such as, e.g., at least 2, at least 3 fold, at least 4 fold, or at least 5 fold increased as compared to the level of IL-12 on day 1 of phase ii).

36. A method according to any of embodiments 31-35, wherein the substance capable of up-regulating IL-12R on the T-lymphocytes, such as, e.g. a substance having agonistic activity towards an interferon receptor is added from day 2 to and including day 4 after initiating the second phase ii), such as, e.g. on day 2, on day 3 or on day 4.

37. A method according to any of the preceding embodiments, wherein the second phase ii) comprises adding one or more substances capable of antagonizing development of Th2 type T-lymphocytes.

38. A method according to embodiment 37, wherein the one or more substances capable of antagonizing development of Th2 type T-lymphocytes are one or more substances capable of neutralizing IL-4, IL-5, IL-10, and/or TGF-beta.

39. A method according to embodiment 38, wherein the one or more substances capable of neutralizing IL-4, IL-5, IL-10, and/or TGF-beta are anti IL-4 antibody, anti IL-5 antibody and/or anti IL-10 antibody.

40. A method according to any of embodiments 37-39, wherein the one or more substances capable of antagonizing development of Th2 type T-lymphocytes, such as, e.g., one or more substances capable of neutralizing IL-4, IL-5, IL-10, and/or TGF-beta is added on day 1 of the second phase ii).

41. A method according to any of embodiments 37-39, wherein the one or more substances capable of antagonizing development of Th2 type T-lymphocytes, such as, e.g., one or more substance capable of neutralizing IL-4, IL-5, IL-10, and/or TGF-beta is added in a subsequent step after addition of the substance capable of up-regulating IL-12R on the T-lymphocytes.

42. A method according to embodiment 41, wherein the one or more substances capable of antagonizing development of Th2 type T-lymphocytes, such as, e.g., one or more substance capable of neutralizing IL-4, IL-5, IL-10, and/or TGF-beta is added one day after addition of the substance capable of up-regulating IL-12R on the T-lymphocytes.

43. A method according to any of the preceding embodiments, wherein a further amount of the one or more substance capable of antagonizing development of Th2 type T-lymphocytes, such as, e.g., one or more substance capable of neutralizing IL-4, IL-5, IL-10 and/or TGF-beta is added regularly throughout phase ii).

44. A method according to embodiment 43, wherein a further amount of the one or more substance capable of antagonizing development of Th2 type T-lymphocytes, such as, e.g., one or more substance capable of neutralizing IL-4, IL-5, IL-10 and/or TGF-beta is added every $2^{nd}$, $3^{rd}$ or $4^{th}$ day of phase ii).

45. A method according to any of the preceding embodiments, wherein a further amount of a substance having agonistic activity towards the IL-2 receptor is added regularly throughout phase ii).

46. A method according to embodiment 45, wherein the substance having agonistic activity towards the IL-2 receptor is added every $2^{nd}$, $3^{rd}$ or $4^{th}$ day of phase ii), such as, e.g., every $3^{rd}$ day.

47. A method according to embodiment 45 or 46, wherein the substance having agonistic activity towards the IL-2 receptor is IL-2.

48. A method according to any of the preceding embodiments, wherein the second phase ii) comprises adding one or more substances promoting the development of Th1 type T-lymphocytes.

49. A method according to embodiment 48, wherein the one or more substances promoting the development of Th1 type T-lymphocytes is substances having agonistic activity towards the IL-7, IL-12, IL-15 and/or IL-21 receptor.

50. A method according to embodiment 49, wherein the one or more substances is selected from IL-7, IL-12, IL-15 and IL-21.

51. A method according to any of embodiments 48-50, wherein one or more substances promoting the development of Th1 type T-lymphocytes, such as, e.g., substances having agonistic activity towards the IL-7, IL-12, IL-15 and/or IL-21 receptor is added when the level of IFN-gamma is increased as compared to the level of IFN-gamma on initiation of second phase ii).

52. A method according to embodiment 51, wherein the increased level of IFN-gamma is determined as at least a 1 fold increase in IFN-gamma level, such as, e.g., at least a 2 fold, at least a 3 fold, at least a 4 fold increase as compared to the level of IFN-gamma on initiation of the second phase ii).

53. A method according to any of embodiments 48-52, wherein the one or more substances promoting the development of Th1 type T-lymphocytes, such as, e.g., substances having agonistic activity towards the IL-12, IL-15 and/or IL-21 receptor is added when CD25 and/or CD69 are down-regulated.

54. A method according to any of embodiments 48-53, wherein the concentration of each of the one or more substances promoting the development of Th1 type T-lymphocytes, such as, e.g., substances having agonistic activity towards the IL-7, IL-12, IL-15 and/or IL-21 receptor added is from about 150 IU/ml culture medium to about 300 IU/ml culture medium, such as, e.g. 250 IU/ml culture medium.

55. A method according to any of embodiment 48-54, wherein the one or more substances promoting the development of Th1 type T-lymphocytes, such as, e.g., substances having agonistic activity towards the IL-12, IL-15 and/or IL-21 receptor is added from day 5 to and including day 8 after initiating the second phase ii), such as, on day 5, day 6, day 7 or day 8.

56. A method according to any of the preceding embodiment for the preparation of CD4+ helper T lymphocytes.

57. A method according to any of the preceding embodiments for the preparation of effector T-lymphocytes.

58. A method according to any of the preceding embodiments for the preparation of memory T-lymphocytes.

59. A method according to any of the preceding embodiments for the preparation of Th1 type T-lymphocytes.

60. A method according to any of the preceding embodiments, which further comprises monitoring the expression of cell surface markers, such as, e.g., CD25 and/or CD69 on the T-lymphocytes continuously during the first phase i) and second phase ii).

61. A method according to embodiment 60, wherein the T-lymphocytes are harvested when CD25 on T-lymphocytes in the second phase ii) is down-regulated.

62. A method according to embodiment 61, wherein the T-lymphocytes are subjected to at least one additional round of phase ii), when CD25 on T-lymphocytes is down-regulated.

63. A method according to embodiment 61 or 62, wherein the down-regulation is defined as that 5% or less of the CD4 positive T-lymphocyte population expresses CD25.

64. A method according to any of the preceding embodiments, wherein the tumour-reactive T-lymphocytes are harvested from day 10 to and including day 14 after initiating the second phase ii).

65. A method according to embodiment 64, wherein the tumour-reactive T-lymphocytes are purified after harvest.

66. A method according to any of the preceding embodiments further comprising a step of freezing the tumour-reactive T-lymphocytes obtained in the second phase ii).

67. A method according to any of the preceding embodiments, wherein the T-lymphocytes are derived from lymph nodes draining a primary tumour and/or a metastasis, or they are derived from blood.

68. A method according to any of the preceding embodiments further comprising a step of freezing the tumour-reactive T-lymphocytes obtained in the second phase ii).

69. A method according to any of the preceding embodiments, wherein the T-lymphocytes are derived from lymph nodes draining a primary tumour and/or a metastasis, or they are derived from blood.

70. A method according to any of the preceding embodiments, wherein the tumour-reactive T-lymphocytes in step iv) are administered intravenously, intraarterially or intrathecally, intraperitonally.

71. A method according to any of the preceding embodiments, wherein the amount of tumour-reactive T-lymphocytes administered is at least 10 million, such as, e.g. at least 20 million, at least 30 million, at least 40 million, at least 50 million, at least 60 million, at least 70 million or at least 80 million.

72. A method according to any the preceding embodiments, wherein the tumour-reactive T-lymphocytes administered are a combination of effector T-lymphocytes and memory T-lymphocytes.

73. A method according to embodiment 72, wherein the percentage of effector T-lymphocytes is from about 10% to about 65%, such as, e.g., from about 20% to about 50% or from about 30% to about 40%.

74. A method according to any of the preceding embodiments, wherein the tumour-reactive T-lymphocytes are autologous.

75. A method according to any of the preceding embodiments, wherein the tumour-reactive T-lymphocytes are non-autologous.

76. A tumour-reactive T-lymphocyte prepared according to the method defined in any of embodiments 1-75.

77. A tumour-reactive T-lymphocyte according to embodiment 76, which is a CD4+ T-lymphocyte.

78. A tumour-reactive T-lymphocyte according to embodiment 76 or 77, which is an effector T-lymphocyte.
79. A tumour-reactive T-lymphocyte according to any of embodiments 76-78, which is a memory T-lymphocyte.
80. A tumour-reactive T-lymphocyte according to any of embodiment 76-79, which is a Th1 type T-lymphocyte.
81. Use of tumour-reactive T-lymphocytes according to any of embodiments 76-80, for the preparation of a medicament for the treatment of disseminated cancer.
82. Kit for use in a method according to any of embodiments 1-75, the kit comprising a media for cultivation of T-lymphocytes.
83. Kit according to embodiment 82 further comprising one or more substances for stimulating, activating and directing tumour-reactive T-lymphocytes.
84. Kit according to embodiment 82 or 83, wherein the media a serum free medium, such as, e.g. AIMV, RPMI 1640, DMEM or MEM.
85. Kit according to any of embodiments 82-84, wherein the one or more substances for stimulating, activating an directing tumour-reactive T-lymphocytes are selected from tumour-derived antigen, substances having agonistic activity towards the IL-2 receptor, substances capable of up-regulating IL-12R on the T-lymphocytes, substances capable of antagonizing development of Th2 type T-lymphocytes and substances promoting the development of Th1 type T-lymphocytes.
86. Kit according to any of embodiments 82-85, wherein the one or more substances for stimulating, activating and directing tumour-reactive T-lymphocytes are selected from the group comprising IL-2, interferon-alpha, anti-IL-4 antibody, anti-IL-5 antibody, anti-IL-10 antibody, IL-7, IL-12, IL-15 and IL-21.
87. Kit according to any of embodiments 82-86, comprising a pharmaceutical composition suitable for intravenous administration.
88. A kit for detection of sentinel or metinel lymph nodes, the kit comprising a syringe and a lymph node locator.
89. A kit for detection of sentinel or metinel lymph nodes, the kit comprising a syringe prefilled with a lymph node locator.
90. Kit according to any of embodiments 82-89 further comprising instructions for use.
91. Kit according to embodiment 90, wherein the instructions are in the form of computer software.

What is claimed is:
1. A method for treating a patient suffering from a neoplastic disease selected from gall bladder cancer, hepato cellular cancer, ovarian cancer, small intestine cancer, lung cancer, mesothelioma, breast cancer, kidney cancer, pancreas cancer, prostate cancer, carcinoid cancer, leiomyosarcoma, or metastasis thereof, the method comprising:
  a) isolating tumour-reactive T-lymphocytes from either the patient's blood, or from the patient's lymph nodes, wherein tumour-reactive T-lymphocytes isolated from the patient's lymph nodes are obtained by:
    i) identifying in a patient one or more sentinel and/or metinel lymph nodes draining a neoplasm selected from gall bladder cancer, hepato cellular cancer, ovarian cancer, small intestine cancer, lung cancer, mesothelioma, breast cancer, kidney cancer, pancreas cancer, prostate cancer, carcinoid cancer, leiomyosarcoma, or metastasis thereof,
    ii) resecting the one or more nodes and, optionally all or part of the tumour or metastasis, and
    iii) isolating tumour-reactive T-lymphocytes from said lymph nodes;
  b) in vitro expanding said tumour-reactive T-lymphocytes isolated from either the patient's blood or lymph nodes using:
    i) a first phase of stimulating tumour-reactive CD4+ helper and/or CD8+ T-lymphocytes with tumour-derived antigen together with at least one substance having agonistic activity towards an IL-2 receptor to promote survival of tumour-reactive CD4+ helper and/or CD8+ T-lymphocytes; and
    ii) a second phase of activating and promoting growth of tumour-reactive CD4+ helper and/or CD8+ T-lymphocytes, wherein the second phase is initiated when a CD25 cell surface marker or IL-2R marker is down-regulated on T-lymphocytes; and
  c) administering the thus obtained tumour-reactive T-lymphocytes to the patient.
2. A method according to claim 1, wherein the one or more lymph nodes are identified by injecting one or more lymph node locators into the patient.
3. A method according to claim 2, wherein the one or more lymph node locators are affinity based.
4. A method according to claim 2, wherein the one or more lymph node locators are non-affinity based.
5. A method according to claim 2, wherein one or more lymph node locators are injected into, above, around, adjacent and/or under the tumour or metastasis.
6. A method according to claim 1, wherein the down-regulation is defined as that 5% or less of the T-lymphocyte population which expresses CD25.
7. A method according to claim 1, wherein the first phase is initiated by adding the at least one substance having agonistic activity towards the IL-2 receptor.
8. A method according to claim 1, wherein the tumour-derived antigen is a denatured homogenate of a tumour.
9. A method according to claim 1, wherein the second phase is initiated by the addition of tumour-derived antigen to the T-lymphocytes for activating tumour-reactive CD25-negative T-lymphocytes.
10. A method according to claim 1 or 9, which further comprises addition to the T-lymphocytes of antigen presenting cells together with the tumour-derived antigen.
11. A method according to claim 10, wherein the antigen presenting cells are irradiated peripheral blood leucocytes containing antigen-presenting B-cells and/or monocytes.
12. A method according to claim 1, wherein the second phase comprises adding at least one substance capable of up-regulating IL-12R on the T-lymphocytes.
13. A method according to claim 1, wherein the second phase comprises adding one or more substances capable of antagonizing development of Th2 type T-lymphocytes.
14. A method according to claim 13, wherein the one or more substances capable of antagonizing development of Th2 type T-lymphocytes are one or more substances capable of neutralizing IL-4, IL-5, IL-10, and/or TGF-beta.
15. A method according to claim 14, wherein the one or more substances capable of neutralizing IL-4, IL-5, IL-10, and/or TGF-beta are anti IL-4 antibody, anti IL-5 antibody and/or anti IL-10 antibody.
16. A method according to claim 13, wherein the one or more substances capable of antagonizing development of Th2 type T-lymphocytes, is added on day 1 of the second phase.
17. A method according to claim 1, wherein the second phase comprises adding one or more substances promoting the development of Th1 type T-lymphocytes.
18. A method according to claim 17, wherein the one or more substances promoting the development of Th1 type

T-lymphocytes is substances having agonistic activity towards the IL-7, IL-12, IL-15 and/or IL-21 receptor.

19. A method according to claim 18, wherein the one or more substances is selected from IL-7, IL-12, IL-15 and IL-21.

20. A method according to claim 1, for the preparation of CD4+ helper T lymphocytes.

21. A method according to claim 1, for the preparation of effector T-lymphocytes.

22. A method according to claim 1, for the preparation of memory T-lymphocytes.

23. A method according to claim 1, for the preparation of Th1 type T-lymphocytes.

24. A method according to claim 1, which further comprises monitoring the expression of cell surface markers, on the T-lymphocytes continuously during the first phase and second phase.

25. A method according to claim 24, wherein the T-lymphocytes are harvested when CD25 on T-lymphocytes in the second phase is down-regulated.

26. A method according to claim 1, further comprising a step of freezing the tumour-reactive T-lymphocytes obtained in the second phase.

27. A method according to claim 1, wherein the T-lymphocytes are derived from blood and wherein the tumour-derived antigen is added essentially at the same time as when phase is initiated or at the most up to 2 days thereafter.

28. A method according to claim 1, wherein the tumour-reactive T-lymphocytes are administered to the patient intravenously, intraarterially or intrathecally, intraperitonally.

29. A method according to claim 1, wherein the amount of tumour-reactive T-lymphocytes administered is at least 10 million.

30. A method according to claim 1, wherein the tumour-reactive T-lymphocytes administered are a combination of effector T-lymphocytes and memory T-lymphocytes.

31. A method according to claim 30, wherein the percentage of effector T-lymphocytes is from about 10% to about 65.

* * * * *

UNITED STATES PATENT AND TRADEMARK OFFICE
CERTIFICATE OF CORRECTION

Page 1 of 1

PATENT NO. : 7,951,365 B2
APPLICATION NO. : 12/147752
DATED : May 31, 2011
INVENTOR(S) : Ola Winqvist and Magnus Thörn It is certified that error appears in the above-identified patent and that said Letters Patent is hereby corrected as shown below:

Claim 31, Column 38, line 18, change "65." to --65%.--.

Signed and Sealed this
Sixteenth Day of August, 2011

David J. Kappos
*Director of the United States Patent and Trademark Office*